(12) United States Patent
Yavuz et al.

(10) Patent No.: US 6,539,074 B1
(45) Date of Patent: Mar. 25, 2003

(54) RECONSTRUCTION OF MULTISLICE TOMOGRAPHIC IMAGES FROM FOUR-DIMENSIONAL DATA

(75) Inventors: Mehmet Yavuz, Irving, TX (US); Harvey Ellis Cline, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 112 days.

(21) Appl. No.: 09/648,957

(22) Filed: Aug. 25, 2000

(51) Int. Cl.⁷ .................................................. A61B 6/03
(52) U.S. Cl. ............................... 378/4; 378/8; 378/901
(58) Field of Search ........................... 378/4, 8, 15, 901

(56) References Cited

U.S. PATENT DOCUMENTS

| | | | |
|---|---|---|---|
| 5,046,003 A | 9/1991 | Crawford | |
| 5,208,746 A | 5/1993 | King et al. | |
| 5,262,946 A | * 11/1993 | Heuscher | ..................... 378/15 |
| 5,291,402 A | 3/1994 | Pfoh | |
| 5,663,995 A | 9/1997 | Hu | ................................ 378/15 |
| 5,991,356 A | * 11/1999 | Horiuchi et al. | ................ 378/8 |
| 5,997,883 A | 12/1999 | Epstein et al. | |
| 6,154,516 A | * 11/2000 | Heuscher et al. | ............. 600/322 |
| 6,353,653 B1 | * 3/2002 | Edic | ................................ 378/4 |

OTHER PUBLICATIONS

"Principles of Computerized Tomographic Imaging", A. C. Kak & M. Slaney, pp. 126–132 (1988).

* cited by examiner

Primary Examiner—David V. Bruce
(74) Attorney, Agent, or Firm—Lester R. Hale; Patrick K. Patnode

(57) ABSTRACT

The invention provides tomographic image generation from four-dimensional projection data of an imaged object. The ability is provided to extract implicit information from time dependent aspects of volumetric projection data corresponding to multiple data acquisition cycles. The result is improved volumetric image quality from volumetric projection data previously used for slice by slice image reconstruction. The invention provides particular advantages for volumetric imaging of a patient's heart, or a portion thereof, at a selected phase of the cardiac cycle.

60 Claims, 14 Drawing Sheets

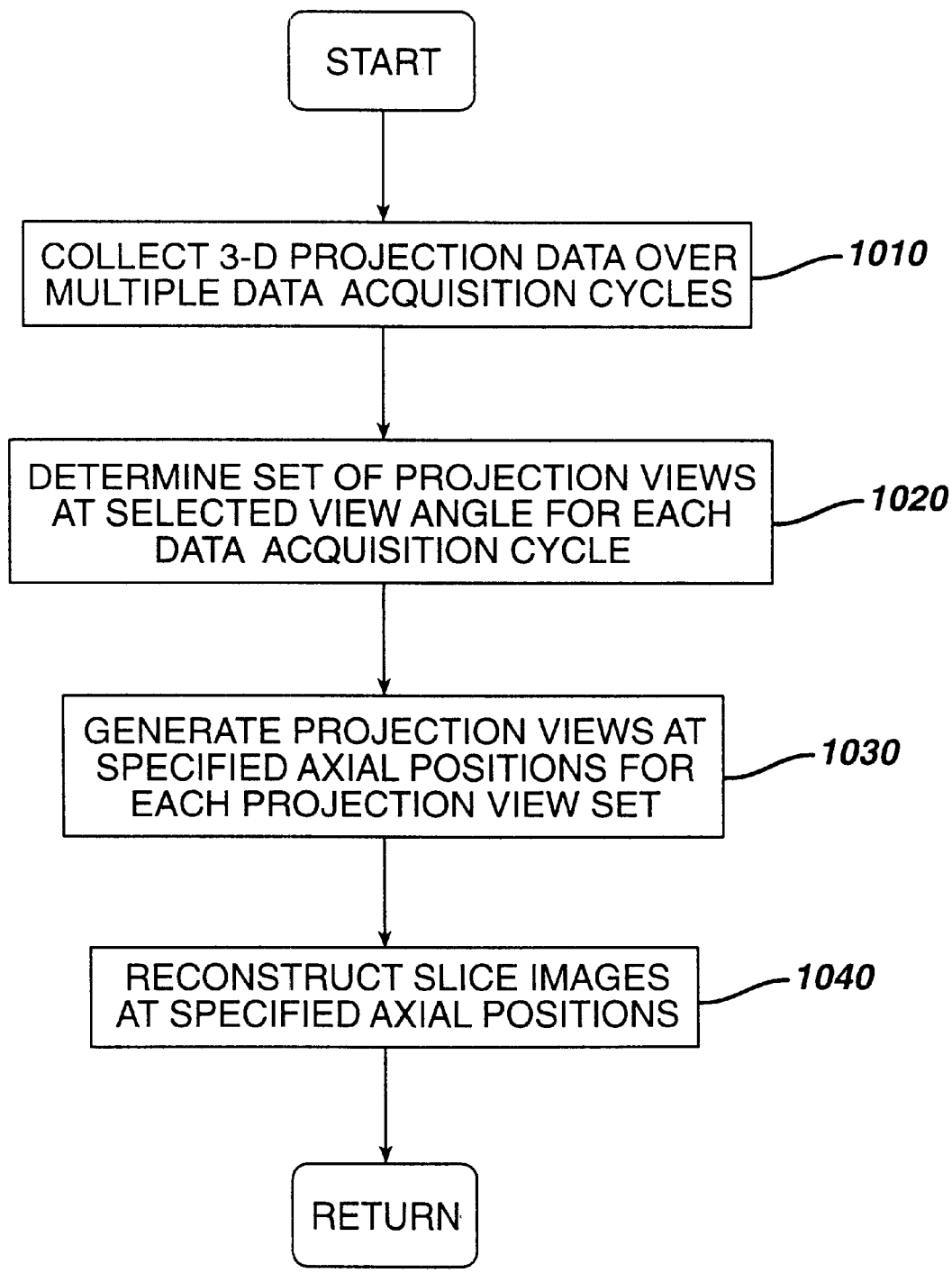

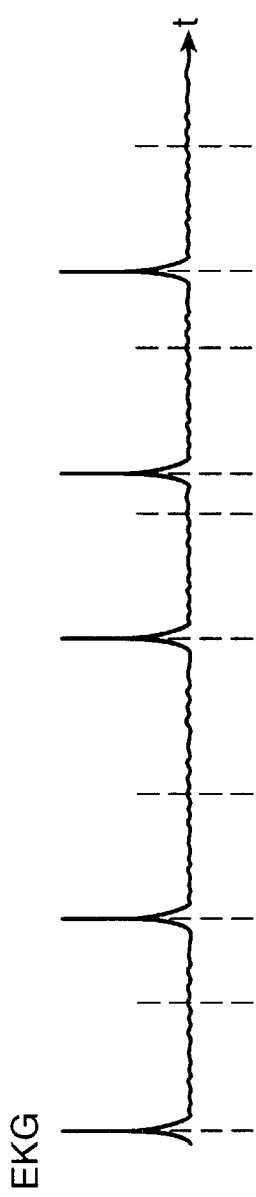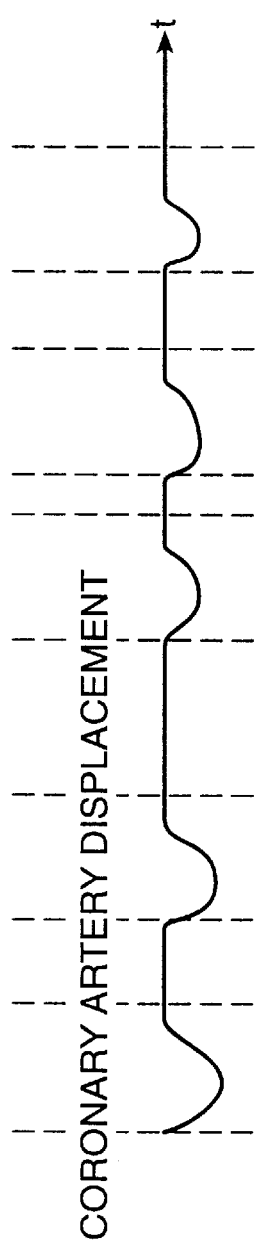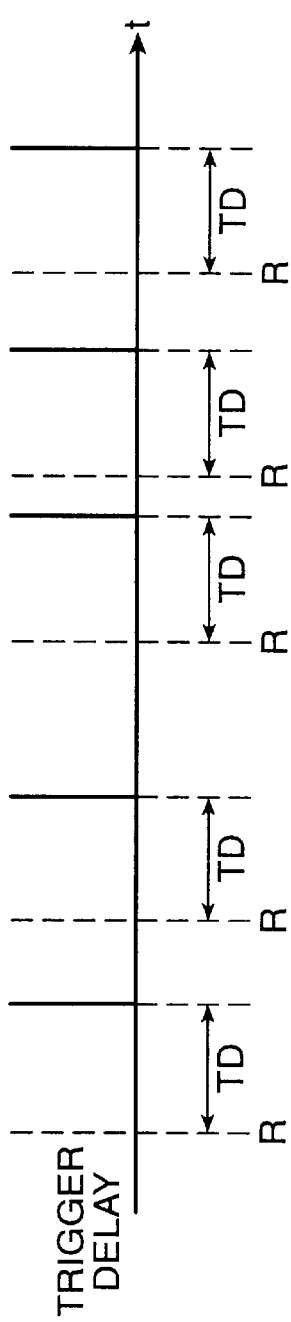

RECONSTRUCTION OF MULTISLICE TOMOGRAPHIC IMAGES FROM FOUR-DIMENSIONAL DATA

BACKGROUND OF THE INVENTION

This invention relates to generation of computed tomographic images. More particularly, the invention relates to reconstruction of multiple, tomographic slice images to represent an imaged object in three spatial dimensions, using four-dimensional tomographic projection data.

Tomography (or computed tomography, abbreviated "CT") is a class of technologies for generating images that accurately represent the interiors of objects. Unlike direct images (such as photographic images, conventional radiographs, etc.), a tomographic image is generated by reconstructing image data from projection data. The "projection data" are data that represent properties of illuminating rays transmitted through the object along numerous non-parallel paths. Reconstruction of the projection data into image data may be carried out through an appropriate computational process for image reconstruction. As used herein, the term "tomographic image" will mean any image generated by a process of tomography. A three-dimensional image of the interior of the object is therefore a "tomographic image," also, if reconstructed from projection data. A tomographic image depicting a cross section of the object is sometimes called a tomographic "slice" image.

Medical applications of tomography have become commonplace and are widely known to provide images of almost photographic detail. A trained physician can draw detailed diagnostic conclusions from a single tomographic slice image. More generally, tomographic imaging has become a useful tool in such diverse areas of application as nondestructive testing, microseismic mapping of underground geological formations, and three-dimensional imaging with electron microscopy.

In the context of medical applications, the challenges of early diagnosis and treatment of disease continue to demand improved assessment methods. For example, serious limitations have continued to exist in the available approaches for assessment of coronary artery disease. Coronary artery disease principally in the form of atherosclerosis leading to vessel stenosis, is a leading cause of myocardial infarction and ischemia.

Several imaging modalities have been available for assessing coronary artery disease. The standard technique for assessment of atherosclerotic stenosis in the coronary vasculature is cardiac catheterization. This technique requires the placement of a catheter in a particular branch of the coronary vessel, injecting a radio-opaque contrast agent while X-ray fluoroscopic images are acquired using an image intensifier or a digital detector array.

Catheterization procedures are effective but are also highly invasive. Moreover, conventional techniques for assessment by catheterization involve acquiring two dimensional (2D) projection images of the 3D vasculature. Hence the data that is acquired may be confounded by structures in the chest or by contortions of the vessels themselves.

Various forms of tomography have been proposed as alternatives to angiographic catheterization. However, most previous efforts in this direction have yielded mixed results, due to issues of image quality. The acquisition of data for accurate tomographic images depends upon the patient being stationary while data is being acquired, to ensure that the acquired data are mathematically consistent. Data inconsistency is well known to create artifacts (such as streaks and blurring) in the resulting reconstructed images. Blurring of image details (such as vessel walls) is a known problem that tends to reduce the effectiveness of the existing approaches to quantification.

The patient's respiration is a source of motion that is readily controlled by acquiring the data during periods when the patient's breath is held (such periods being called "breath-holds"). However, unlike other organs, the beating heart undergoes motion even during breath-holds. Effective data acquisition for tomographic imaging therefore calls for measures to compensate for the concurrent motion of the heart.

Magnetic resonance (MR) imaging has been implemented with special data acquisition protocols that provide some compensatory measures. The acquired data can be reconstructed to generate a three-dimensional (3D) representation of the relevant structures of the subject's heart. The coronary vasculature may be segmented from the myocardium, whereby vascular stenosis may then be quantified by conventional techniques.

On the other hand, a basic problem with generating volumetric images of cardiac structures is to address simultaneously four competing data collection criteria. First, generating a volumetric representation of a cardiac structure entails acquiring sufficient projection data for reconstruction of a plurality of stacked slice images, or else for a three-dimensional reconstruction. Second, the spatial resolution and fidelity of the reconstructed image data are directly tied to the number of distinct projections in the acquired projection data. Hence, reconstructing usable images entails acquiring numerous projections. Third, because the heart is in motion during the data acquisition, the acquired data variously represent the heart in all different phases of the cardiac cycle. Reconstruction of an accurate three-dimensional representation thus entails some form of cardiac gating in the data acquisition process, so that the projections used to reconstruct the image data all represent the heart structures at approximately the same phase of the cardiac cycle. Fourth, shorter data acquisition times are more desirable to minimize the patient's discomfort, the radiation dose (for CT scans using ionizing radiation), and motion blur due to respiration or multiple breath-holds.

Existing cardiovascular MR techniques have simultaneously addressed at most three of these four criteria. Effective study of the coronary vasculature has depended upon images with high resolution and high fidelity. To obtain sufficient data with existing techniques, the data acquisition time for a three-dimensional representation can amount to several minutes and has entailed both respiratory gating and cardiac gating. U.S. Pat. No. 5,997,883 to Epstein, et al., notes that generation of multiple slice images from conventional spin echo sequence data results in slice images representing the heart at different phases of the cardiac cycle. The same patent describes methods for generating time-lapse (i.e., "cine") images by using short repetition times and retrospective data resorting to bin the data according to cardiac phase. However, such methods are specifically directed toward imaging the time evolution of the heart at a single spatial location and thus are not readily applicable to volumetric imaging.

X-ray tomography (XCT) has also been considered for assessment of cardiovascular disease. Recent developments in image reconstruction algorithms have improved this situation somewhat by enabling CT techniques to achieve better time resolution than with the standard operation mode. The basic approach of these techniques has been to segment consistent projection data collected from multiple heart cycles based on predetermined sectors of the cardiac cycle. Such data sectoring methods have been shown to improve significantly the time resolution of the collected data. In practice, however, these existing methods have been found to introduce some image artifacts due to inconsistencies in the data.

On the other hand, it would be desirable to generate three-dimensional images using as much information as possible from the volumetric projection data.

It is therefore apparent that a continuing need exists for an efficient technique to generate three-dimensional images from volumetric projection data.

Such a method desirably would provide acceptable spatial resolution in the resulting images, without requiring extensive additional data acquisition. In imaging contexts where the imaged object is in motion, such as in cardiac imaging, the method would desirably overcome the artifact problems that have existed with data segmentation methods. Preferably, the technique would be flexibly applicable in a broad range of CT imaging contexts.

BRIEF SUMMARY OF THE INVENTION

In a first aspect, the invention provides a method, device, system, and software for tomographic image generation. A method of this first aspect may comprise determining plural sets of projection views of an object based on projection data from respective different data acquisition cycles. Each set comprises plural projection views of the object at a corresponding view angle and at successive positions on an axis. A slice image of the object is reconstructed at a specified position on the axis based on a plurality of projection views selected from respective ones of the plural sets.

In a second aspect, the invention provides a method, device, system, and software for tomographic image generation. A method of this second aspect may comprise determining plural sets of projection views representing an object in a predetermined phase of repetitive motion in respective different data acquisition cycles. Each set comprises plural projection views of the object at respective axial positions. A plurality of adjacent slice images of the object are generated based on the plural sets of projection views.

In a third aspect, the invention provides a method, device, system, and software for tomographic cardiac imaging. A method of this third aspect may comprise generating a plurality of x-ray projection data sets based on detector data collected in respective different data acquisition cycles. Each projection data set comprises plural projection views of a subject's heart at a corresponding view angle and at successive positions on an axis of rotation through the subject. A plurality of stacked slice images are reconstructed based on respective projection view sets each comprising projection views selected from respective ones of the projection data sets. Each slice image represents the patient's heart at a corresponding position on the axis. The plurality of stacked slice images together depicts at least a three-dimensional portion of the subject's heart.

BRIEF DESCRIPTION OF THE DRAWINGS

These and other aspects and advantages of the invention will become apparent and more readily appreciated from the following detailed description of the preferred embodiments, taken in conjunction with the accompanying drawings of which:

FIG. 10 is a flow diagram illustrating a procedure of the invention for cardiac imaging;

FIG. 11 is a time evolution diagram of detector row positions of a multi-row detector in relation to the trigger delays shown in FIG. 9C;

DETAILED DESCRIPTION OF THE INVENTION

The present invention implements a different perspective on three-dimensional tomographic projection data, whereby a broader range of information contained in the data is recognized and used. Previous approaches to processing three-dimensional projection data have processed the raw volumetric data to obtain individual slice images.

However, previous methods for processing projection data have failed to recognize that additional information about the imaged object may exist in relationships between three-dimensional projection data representing the object at different slice locations. Such additional information may arise, for example, when the three-dimensional data are obtained over plural data acquisition cycles. An aspect of the invention comprises a recognition that such additional information potentially exists and may be used to enhance the image quality of the resulting tomographic images.

In a preferred embodiment, the present invention provides an improved processing method that achieves the objectives of previous data rebinning approaches for CT projection data collected from multiple cardiac cycles, while avoiding many of the image artifacts that have accompanied such previous approaches. The result of the invention is improved image quality and reduced artifacts for reconstructed images at arbitrary heart phases.

Figure 1:
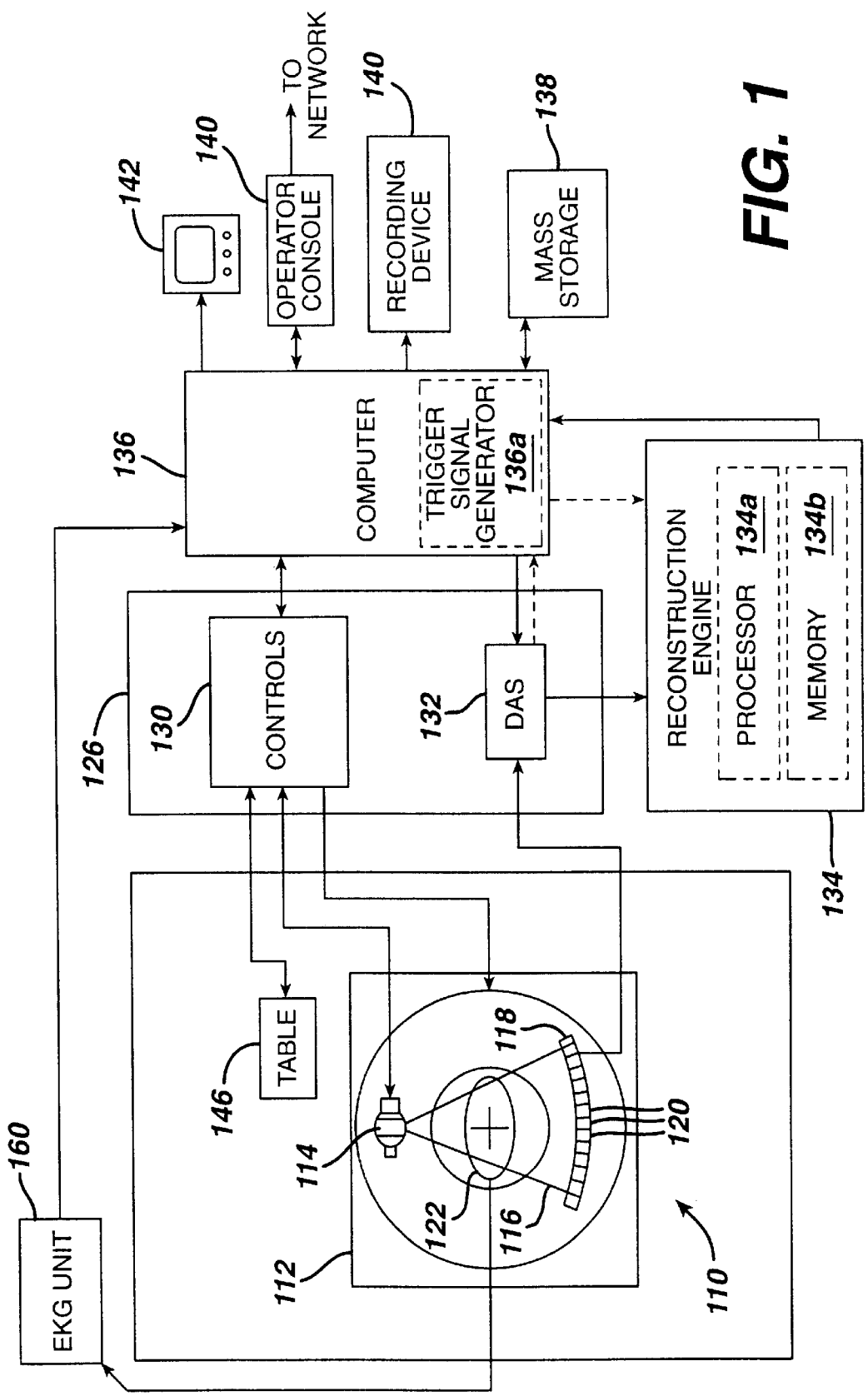
FIG. 1 is a block diagram of a general x-ray CT scanning system in which the present invention may be implemented.

FIG. 1 is a schematic illustration showing the major components of an x-ray tomographic imaging system 100 in which the present invention may be incorporated. The system 100 desirably comprises a source-detector assembly 110, which in an exemplary embodiment may comprise a gantry 112. An X-ray source 114, such as a typical X-ray tube, is mounted on the gantry 112 and rotates with rotation of the gantry 112. Source 114, which may comprise a collimating element (not shown), projects a beam 116 of x-rays toward a detector array 118 disposed opposite the source 114 relative to the gantry 112. The beam 116 may comprise a thin, fan shaped beam of radiation. Hence, "thin" here refers to the direction transverse to the fan plane. Alternatively, as explained below with reference to FIG. 7, the beam 116 may be a so-called "cone" beam extending substantially in two perpendicular directions.

The detector array 118 is typically comprised of numerous individual detector elements 120. An alternative term in the art for an array such as detector array 118 is "a multi-channel detector." It will be understood that either term is intended to mean a multiple-channel detection device usable in a computed tomography system.

Detector elements 120 together provide information regarding the internal structures of a subject 122. In the typical medical application of CT scanning, the subject 122 is a human patient undergoing medical evaluation or testing. Alternatively, in a veterinary context, the subject 122 may be an animal patient. In either of these cases, an organ or body part may be the object 124 of interest and thus is the "object" for purposes of the tomographic image. In a still further alternative application, the subject 122 may itself be an inanimate object being subjected to, for example, nondestructive testing or examination.

In any case, each detector element 120 generates a signal indicating the intensity of a portion of the x-ray beam 116 impinging thereupon. The signals from detector elements 120 indicate the attenuation of the beam 116 as the x-rays traverse the material of the subject 122. Typically the source 114 is rotated around the subject 122 during a scan operation to acquire x-ray data. Rotation of the source 114 may be implemented by rotation of the gantry 112 and the components mounted thereto (including the source 114).

The rotation operation for the source 114 is controlled by a control/interface system 126. A controls section 130 of the control/interface system 126 provides control for both positioning (such as gantry speed and position) and x-ray generation (power and timing) of the source 114. The control/interface system 126 also includes a data acquisition system (DAS) 132 that samples analog data from the detector elements 120 and converts the sampled data into digital data for further processing.

A reconstruction engine 134 receives the sampled and digitized data (now termed "projection data") from the DAS 132 and performs high-speed image reconstruction. The reconstruction engine 134 may comprise a separate processor 134a and memory 134b. Various algorithms are known in the art for reconstructing a slice image from projection data comprising a plurality of projection views. The reconstruction engine 134 sends the reconstructed image to, for example, a system management computer 136 for storage or display. Computer 136 may store the image in a storage 138, preferably as a data array.

The different functions of control/interface system 126, reconstruction engine 134, and computer 136 are desirably implemented on dedicated modular platforms, as described. However, the division of functions described herein is for purposes of example and is not intended to be limiting. Such functions may alternatively be implemented in software, on a single computational platform, or in a different arrangement on multiple hardware platforms.

The computer 136 also receives commands and scanning parameters through an operator console 140. Output of the reconstructed image, as well as operational data and other information, may be performed through a video display 142 (such as a CRT display, flat panel display, etc.). The reconstructed image may optionally be directed to a recording device 144, such as a film recorder. Alternatively, the image may be transmitted as image data over a network (not shown) for disposition at another location.

Commands and parameters may be supplied through the console 140 to provide control signals and other information to the control/interface system 126. Further control of the imaging process is achieved by positioning the subject 122 on a motorized table 146 under the control of signals from control/interface system 126. In a typical embodiment, translation of the table 146 moves the subject 122 relative to the source 114 and detector array 118 within a subject aperture 148.

The subject 122 may be a human patient, and the system the system 100 may be used to perform tomographic imaging of the patient's beating heart. In this case contemporaneous timing information may be helpful for correlating the collected projection data and the various phases of the heart cycles during which the projection data are collected. Such timing information may be obtained through an EKG unit 160, which typically receives signals from sensors on the patient's body. Based on the sensor signals, electrocardiographic data may be provided by the EKG unit 160 to the computer 136, for example.

The electrocardiographic data provided to the computer 136 may represent, for example, a digital electrocardiogram. As is well known, an electrocardiogram is a recording of electrical activity of the heart as indicated by signals obtained from sensors contacting the patient's body. The EKG unit 160 thus may comprise an electrocardiograph, which is an instrument for obtaining an electrocardiogram.

To identify projection data corresponding to a particular phase of the heart cycle, a trigger signal generator 136a may process the electrocardiographic data to generate a repeating trigger signal synchronized with the occurrence of the desired phase. The trigger signal generator 136a may be implemented, for example, in the computer 136 or in the EKG unit 160. In the usual manner, such a signal generator may be implemented either in software or in dedicated hardware.

Figure 2:
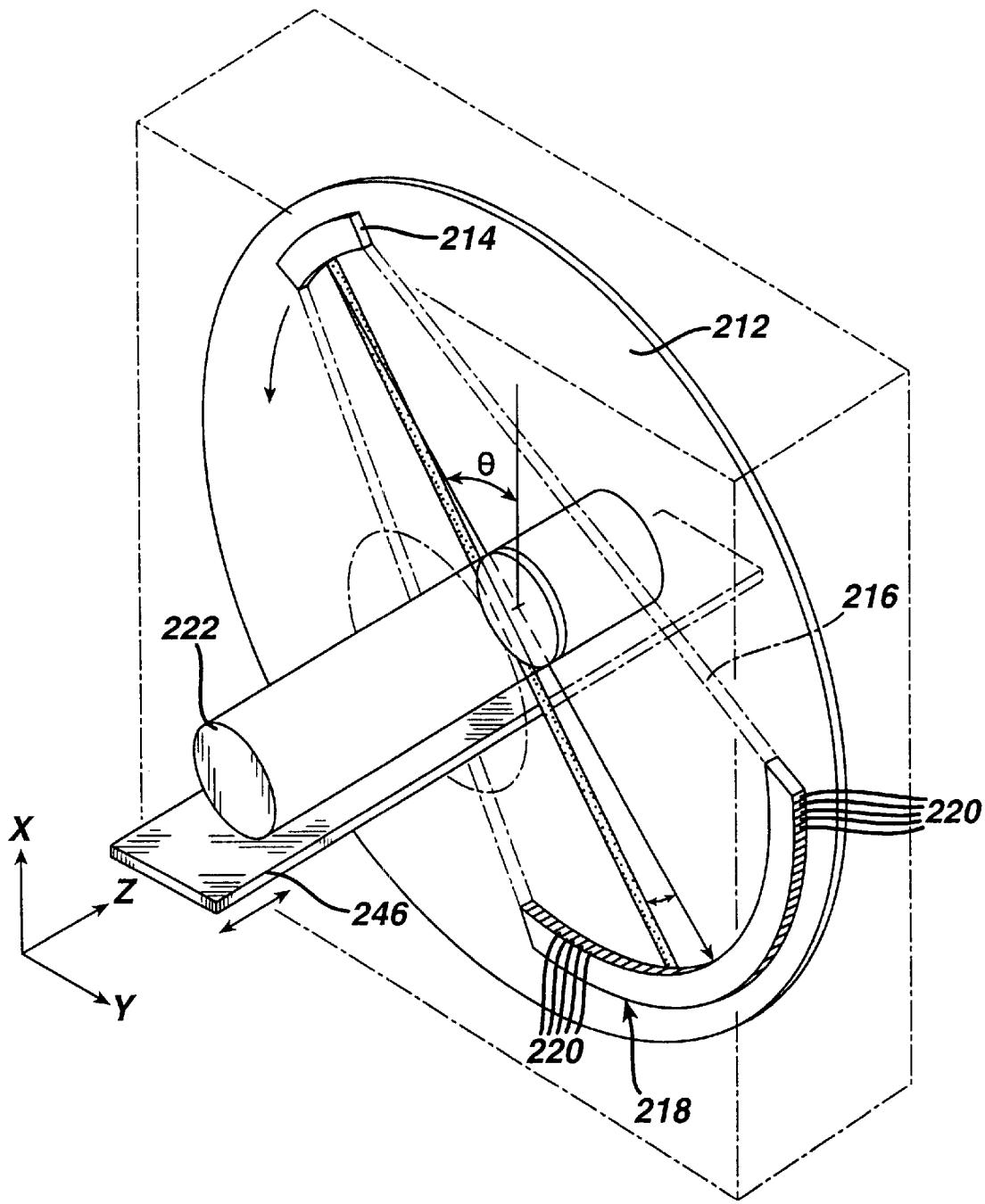
FIG. 2 is a diagram of a third generation source detector assembly for a CT scanning system as shown in FIG. 1.

FIG. 2 illustrates a source-detector assembly 210 as a specific embodiment of the source-detector assembly 110 shown schematically in FIG. 1. Assembly 210 illustrates the particular case of a so-called third generation, fan beam CT system. In the assembly 210, a gantry assembly 212 corresponds to the gantry 112 of FIG. 1. An x-ray source 214 generates a fan beam 216 of x-rays directed toward a detector array 218, which is also affixed to the gantry assembly 212. Array 218 comprises individual detector elements 220 that detect x-rays emitted by source 214. The subject 222, table 246, and subject aperture 248 correspond to subject 122, table 146, and aperture 148 as described with respect to FIG. 1.

In operation, assembly 212 rotates around an axis Z passing through subject 222 and perpendicular to the plane XY. Source 214 can thereby be transported completely around subject 222 along a circular path. Detector array 218, being fixed with respect to source 214, is also transported around subject 222 and thus remains opposite source 214.

Rotation of the gantry assembly 212 around the subject 222 results in x-ray data being generated by detector elements 120 for a range of view angles θ. A typical detector array 212 may comprise several hundred individual detector elements 220, such as 888 individual elements 220. The array 218 is positioned on the gantry 212 at a distance of, for example, 0.949 meter (m) from the source 214. The circular path of source 120 has a radius of, for example, 0.541 m. Particular values of these parameters are not critical to the present invention and may be varied according to well-known principles of CT system design.

One complete gantry rotation for the gantry 212 may comprise, for example, 984 increments. Source 214 is thereby positioned to illuminate the subject 222 successively from 984 different directions θ. Detector array 218 generates x-ray data at each incremental position θ, from which projection data for 984 projection views may be generated.

Figure 3:
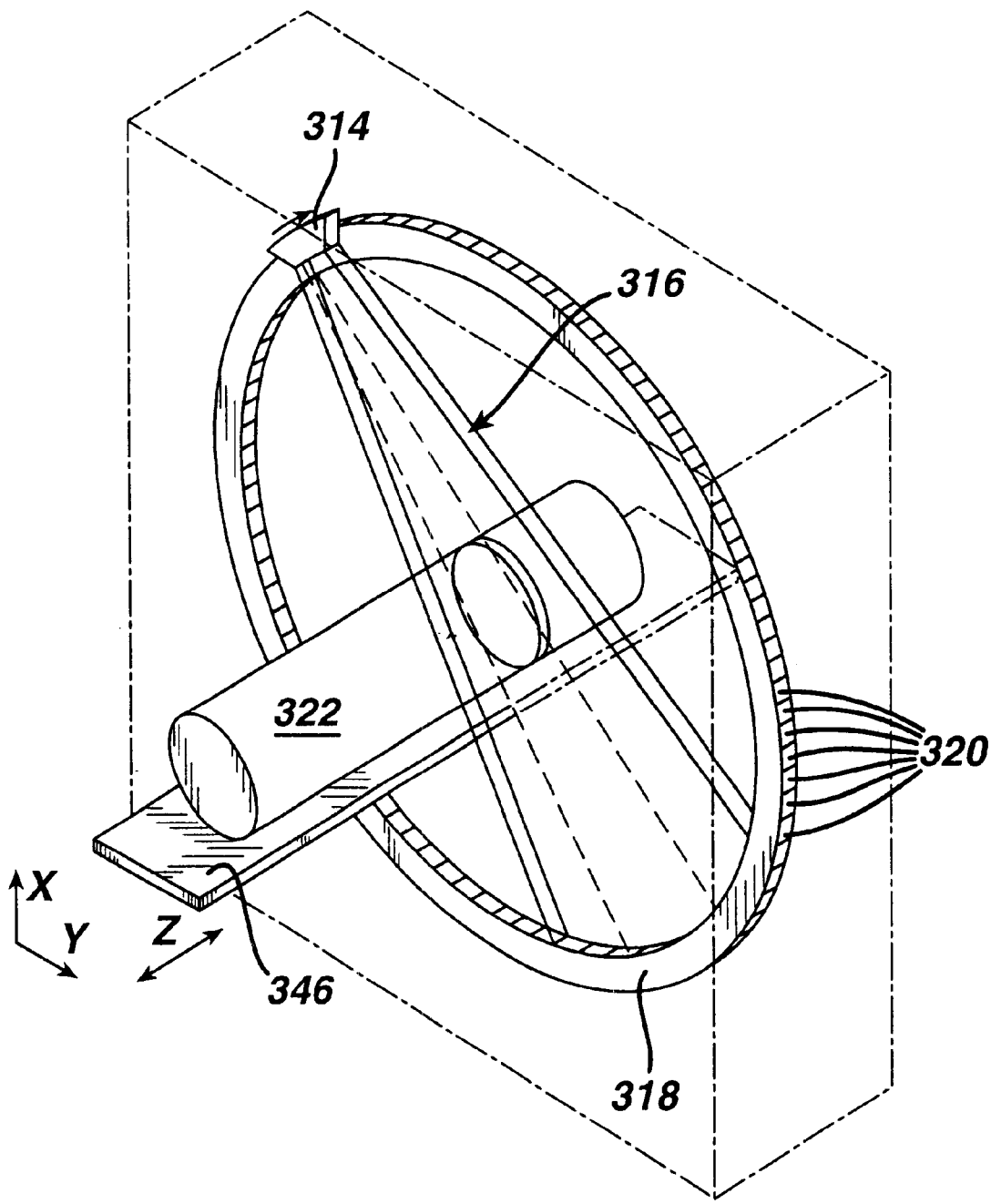
FIG. 3 is a diagram of a fourth generation source detector assembly for such a CT scanning system.

FIG. 3 illustrates a source-detector assembly 310 for a so-called fourth generation fan beam CT system. An x-ray source 314, like source 214 and as a further example of source 114, generates a fan beam 316 of x-rays directed toward a detector array 318. The array 318 comprises detector elements 320 that generate x-ray data indicating internal structural information about a subject 322.

The fourth generation case of FIG. 3 differs from the third generation case, in that the detector array 318 is fixed with respect to rotation. The source 314 is supported by a suitable guide mechanism (not shown) and traverses a circular path around the subject 322. The detector array 318 may translate axially (in the Z direction) to provide x-ray data for a particular axial slice 350. Alternatively, the array 318 may be fixed axially as well as rotationally, and positioning of the subject 322 may be achieved by axial translation of a table 346.

The present invention provides an approach for enhancing resolution and image quality of a CT image without requiring additional detectors or additional data acquisition. The present invention applies to both third generation and fourth generation axial CT systems. The invention may also be used with less advanced (e.g., first or second generation) source-detector arrangements. Moreover, as will be explained below, the invention applies to both axial and spiral (i.e., helical) CT imaging systems. The basic features of the invention will be explained first in the axial CT context and then extended, with appropriate enhancements, to the helical case.

As FIGS. 2–3 show, a typical fan bean CT imaging system executes a cycle of data acquisition by a complete rotation of the gantry around the subject being imaged. The detector data are collected as the gantry rotates the source and the detector array together. The projection data are thereby generated for different angular positions (i.e., view angles) of the gantry. A fourth generation fan beam system, comprising an arrangement such as the assembly 310, shown in FIG. 3, differs in that the detector array is stationary with respect to the subject. Instead, the source rotates and thereby projects imaging rays through the object at different angles for detection by different portions of the fixed array.

It is noted that similar operations of rotation apply in both cases for the acquisition of detector data during a complete cycle of the source-detector assembly. The principle of a rotational cycle of data acquisition is generally applicable in all such x-ray CT scanning systems. Accordingly, "scanning rotation" will be used here to mean the rotational operation for positioning the x-ray source (e.g., source 214 or source 314) at each angular position θ around an axis of rotation and collecting corresponding data. "Scanning rotation set" will mean the set of projection data generated from a scanning rotation. Where no confusion will arise, the term "scanning rotation" will be used variously to mean either the data acquisition operation or the projection data set generated as a result of the data acquisition operation.

Furthermore, typical x-ray CT systems (e.g., third generation systems and fourth generation systems) are an exemplary class of tomographic imaging systems. For example, magnetic resonance imaging (MRI) systems also are used to generate tomographic images by computed tomography. Cardiac imaging can be performed with some MRI systems by processing a series of magnetic echo data sequences with various types of gating techniques.

In MR cardiac imaging by prospective spin echo gating, for example, the system acquires imaging data over a series of cardiac cycles. An additional sequence of spin echo data is acquired at each cycle. Each spin echo data sequence represents the heart at different spatial locations but is acquired during the same cardiac cycle and with the same k-space encoding value. Thus, the data collection operation for acquiring such a spin echo data sequence is analogous to the scanning rotation operation in x-ray tomographic imaging. In each case, the operation is a data sampling cycle for acquiring a consecutive sequence of data samples over a cycle interval.

Also, retrospective gating of gradient echo pulse sequences is used in MR systems to acquire "cine" images at multiple time frames of the cardiac cycle. Data acquisition again occurs over several cardiac cycles, and in each acquisition cycle the data samples have the same phase (i.e., k-space) encoding value. The phase encoding value is thus stepped to a next value at each successive R-wave trigger. The excitation pulses run asynchronously with the cardiac cycle, so that the echo pulse data acquired in each sampling cycle is resorted and interpolated into evenly distributed time frames within the cardiac cycle. Nevertheless, like rotational scanning in x-ray systems, the sample data are again acquired in a series of sequences of data samples acquired consecutively over a sampling cycle interval.

These examples illustrate a general principle of data acquisition in tomographic imaging systems: the imaging data are acquired in one or more sequences of data samples. Here, the term "data acquisition cycle" will mean a data acquisition operation for obtaining such a sequence of data samples at a sequence of consecutive sampling times. Thus, in existing approaches to x-ray tomography the data acquisition cycle is the scanning rotation (which may be carried out by gantry rotation or source rotation, for example). For MRI systems, the data acquisition cycle may be the sequence of measurement operations in which the magnetic field gradients are varied according to the particular localization method being used. As will be explained in detail, the present invention adopts a different perspective on combining data from different data acquisition cycles.

In the fan beam case, the data acquisition cycle is sometimes called an axial scan. The projection data for an axial scan all represent the imaged subject at a same axial position $z_0$. Data from an axial scan may be stored in a two dimensional array called a "sinogram." One dimension of the sinogram corresponds to angular position of the fan beam (e.g., scanning rotation angle or "view angle" θ). The other dimension corresponds to positions of the detector elements (R) of the detector array. The detector array in a fan beam CT system (array 218 of FIG. 2 or array 318 of FIG. 3) generally comprises a single row of detector elements. Therefore, each row of the sinogram corresponds to a discrete view angle θ and a single axial position $z_0$.

A sinogram obtained from an axial scan may itself constitute a collection of projection views of the subject at the position $z_0$. Here the term "projection view" means such a row of projection data corresponding to a given view angle θ and representing the imaged subject at a single axial position $z_0$. Well known reconstruction procedures utilize as their principal inputs a complete set of such projection views (discretized in θ, but all consisting of data values for the same axial position $z_0$). The projection views are processed to generate a slice image depicting the internal features of the subject at the position $z_0$.

Figure 4A:
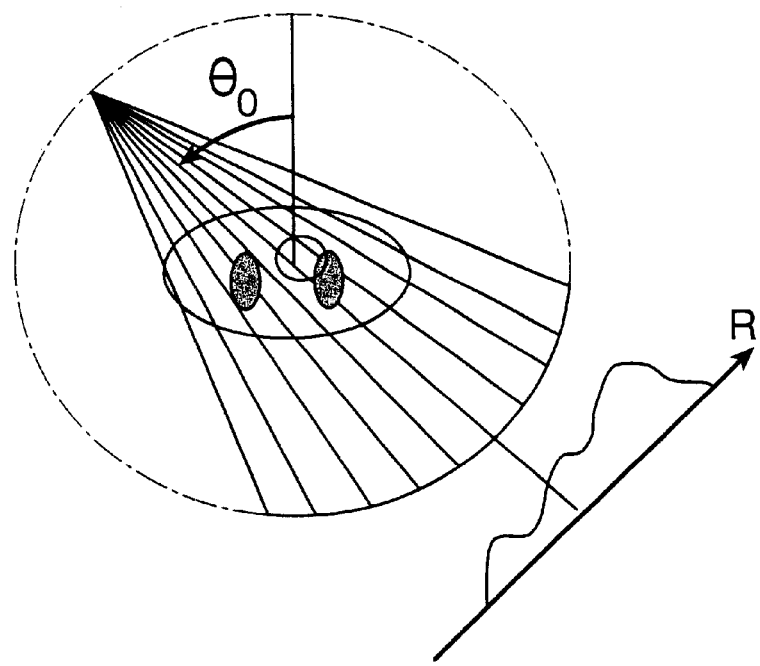
FIG. 4A is a diagram illustrating the correspondence between a particular view angle and generation of a row of projection data.

FIG. 4A illustrates the correspondence between a particular view angle $θ_0$ for the source and the generation of a well defined row R of projection data. In the fan beam case, as noted above, the detector data from the detector array may convert directly into a single row of projection data for a projection view at view angle $θ_0$. This correspondence results because the detector array provides a single row of detector data representing intensities of the x-rays impinging upon the detector elements. These intensity values indicate attenuation information for the subject at the axial position $z_0$.

Figure 4B:
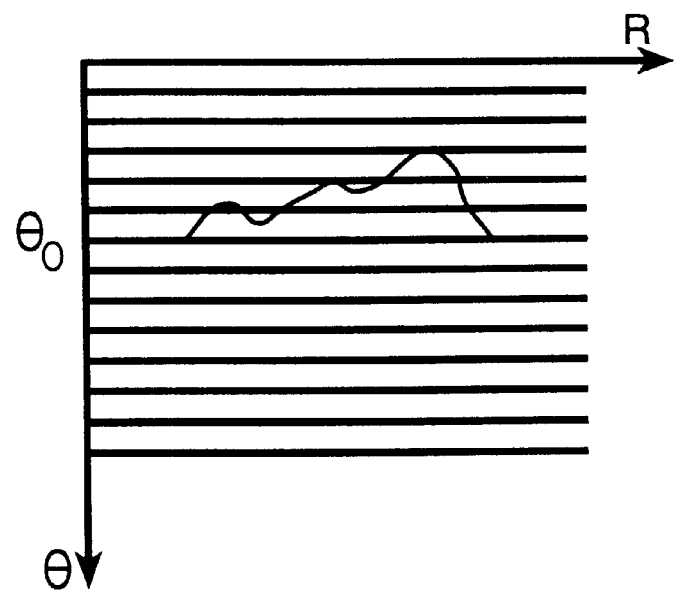
FIG. 4B is an illustration of a sinogram of projection data including the row of projection data of FIG. 4A.

FIG. 4B shows how the projection data for the particular view angle $θ_0$ is stored in a corresponding row of the sinogram. Each row of the sinogram thus constitutes a projection view that indicates attenuation information for a distinct view angle θ, but the same axial position $z_0$. Once the sinogram is filled with projection views (rows) for all the discrete view angles θ around the subject, then a suitable CT image reconstruction algorithm is applied to reconstruct a cross-sectional image of the subject.

Figure 5:
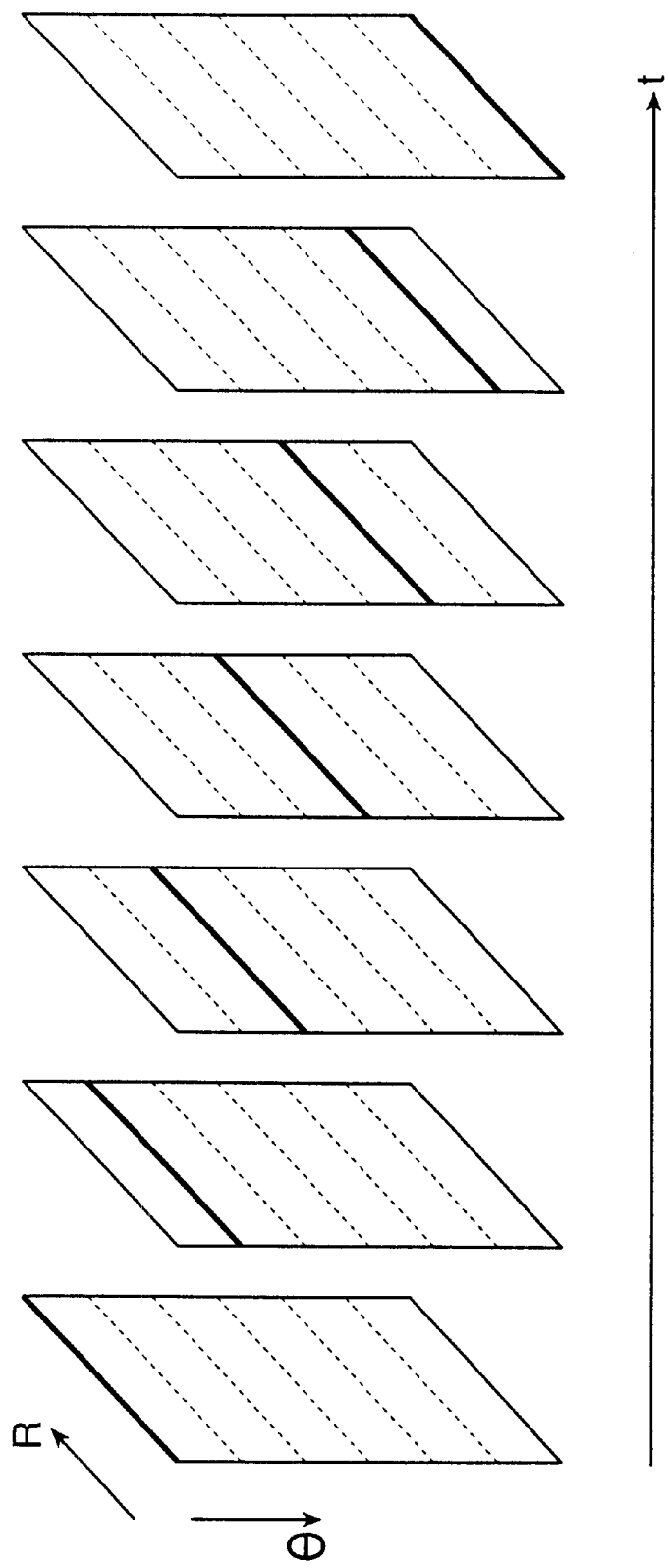
FIG. 5 is a diagram illustrating a time dependent feature of sinogram data.

FIG. 5 illustrates a time dependent feature of the projection data stored in the sinogram. The view angle θ of the source relative to a fixed direction can be written as $$θ(t)=ωt,$$

where ω represents the angular speed of the gantry in radians per second and t denotes time. Each row R of the sinogram therefore represents information about the subject (at the axial position $z_0$) at a different time t.

Usually the fact that the rows of the sinogram are time dependent is inconsequential, because the subject is immobile during the scanning process. The assumption of stasis may be reasonable even for a living patient, because the patient can be well constrained during the time it takes to collect all the projection views (0.5–0.8 seconds). For example, when the area of interest is the patient's head, abdomen, etc., the body part of interest can be assumed to be stationary during the scan.

However, in cardiac imaging the assumption of stasis clearly does not apply, at least for a living subject, because the heart persistently beats. For example, a heart rate of 72 beats per minute (bpm) corresponds to 0.83 seconds (s) per beat. The heart thus completes a full cardiac cycle in a time span comparable to the time span for collecting projection views at all the view angles θ. In effect, the beating heart undergoes motion while the scan data are being collected.

The particular motion that affects cardiac CT imaging is largely the cyclical change in the shape of the heart throughout the cardiac cycle. However, the same imaging problem appears in any situation where the subject is in motion during the CT scan process. The scanner is unable to generate a clear image of the subject being imaged at a particular position (e.g., a particular phase of the cardiac cycle) because the subject moves too rapidly for a complete set of image data to be collected while the subject is in the desired position or configuration.

The problem may be analogized to the problem in conventional photography of freezing a subject in motion. If the camera shutter speed is too slow, the subject will undergo a significant amount of motion while the shutter is open (i.e., collecting image data). The resulting image of the subject is blurred. In a like manner, the CT scanning system may be unable to generate a clear slice image, if the subject is in motion while the scan data are being collected. In effect, the CT scanner has a slow shutter speed relative to most rates of motion of the subject.

FIG. 5 thus illustrates that the collection of projection data proceeds as a function of time while the gantry or source is rotating. A projection data set consisting of projection views for a single, complete scanning rotation ($0°≦θ≦360°$) therefore includes numerous projection views that represent the heart at all the different phases throughout the cardiac cycle. Each projection view corresponds to a particular row in the sinogram, but is collected at a different instant in time. Strictly speaking, reconstruction of an image at any particular phase of the heart would entail collecting all the projection views to be used (all rows of the sinogram) at that particular instant in time. This would require a very fast data acquisition cycle (i.e., a very fast shutter speed for the CT scanning system).

A feasible solution to this problem can be achieved by making use of the cyclical nature of the cardiac cycle. As the cycle repeats, the beating heart moves through the same cycle of shapes and assumes successive shapes in an ordered sequence in time. Multiple scanning rotations, together with data gating, can be used to collect several projection views from multiple heart cycles. The CT scanning system can thereby generate the projection views to be used in reconstructing an image of the beating heart at a particular heart phase.

As indicated above, projection views from multiple heart cycles may be correlated to a particular heart phase by cross-referencing to contemporaneous timing information. The EKG unit 160 shown in FIG. 1, for example, may generate electrocardiographic data indicating timing of the various phases of the cyclical motion of the beating heart. The electrocardiographic data may thus provide timing information by which the projection views may be correlated or cross-referenced to the heart phases in the successive cardiac cycles.

Unfortunately, actually collecting all the desired scan data would entail an inordinately large number of scanning rotations for the corresponding projection views. The "shutter speed" problem arises here in a different form: although the heart regularly repeats the cardiac cycle, the subject being imaged otherwise desirably remain stationary throughout the data collection process. A reasonable number of scanning rotations, during which the subject can be expected to remain generally stationary, will provide just a few projection views of the heart at a given phase.

Figure 6:
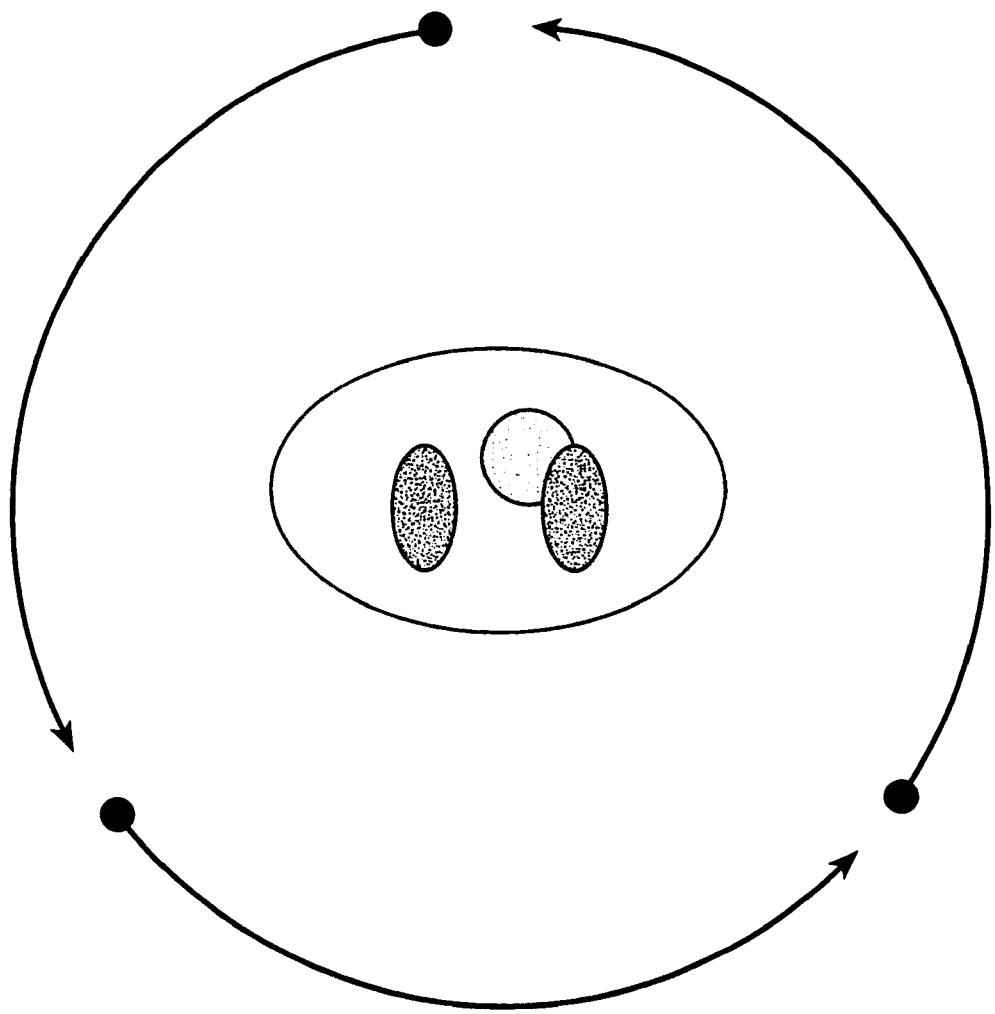
FIG. 6 is a schematic diagram illustrating a sector approach for rebinning data in cardiac imaging applications.

FIG. 6 illustrates this problem through a simplified example in which three projection views are collected at the desired heart phase, $t=t_0$. The three views correspond sequentially to heart cycles 3, 1, and 2 as shown and may be collected in, for example, three scanning rotations. At 0.5 s per scanning rotation, even this level of data collection requires the patient (the imaged subject) to remain stationary for at least 1.5 s.

The following scheme has been partially successful in overcoming the persistent problem of missing projection views in the context of cardiac imaging. An assumption is made that, at least for some phases $t_o$ of the cardiac cycle, the heart motion may be relatively slight in the neighborhood of $t=t_o$. As shown in FIG. 6, the scanning rotations are divided into a few angular sectors. The heart is assumed to be close to stationary in each sector.

The sectors of each scanning rotation can be associated with distinct phases of the heart cycle. Data for different projection views are collected at each scanning rotation. If the foregoing assumptions are valid, then the data collected in the $t_o$ sectors from all scanning rotations can be used for reconstruction of an image of the heart at the $t_o$ phase.

The approach described above has been termed data "sectoring" or "data segmentation" and has been implemented successfully in various contexts. For example, U.S. Pat. No. 5,997,883, issued Dec. 7, 1999, to Epstein et al. and assigned to the assignee of the present application, discloses a cardiac imaging technique using segmented MRI cardiac data. Moreover, data segmentation has been shown to yield x-ray CT images with reasonably good image quality. However, such CT images suffer from certain noticeable artifacts, such as streaks. The artifacts in these images are believed to be due to inconsistency of the projection data, particularly in the regions of transition between the different sectors.

In the case of cardiac imaging, the cardiac R-R interval duration is typically different from the period of the data acquisition cycle (e.g., the duration of a complete gantry rotation). Thus projection views obtained at a given view angle but in different data acquisition cycles typically represent the heart at different phases of the cardiac cycle. Interpolation allows a projection view for a given phase and view angle to be synthesized from existing projection views at the same view angle but representing the heart at somewhat different phases.

The foregoing improved technique has been found to make the resulting projection data (initial projection data in combination with interpolated projection data) more consistent. The enhanced consistency is particularly evident in the regions where multiple sectors are merged. The improved technique has been found to provide distinctly improved image quality, because image artifacts related to data inconsistencies are substantially reduced. In an implementation for cardiac imaging, the technique enables reconstruction of a single slice through the heart with fine resolution in time.

On the other hand, anticipated new uses of tomographic imaging (such as for assessment of vascular stenosis) involve reconstruction of multiple adjacent slices. Typically in such applications it is desired to generate a three-dimensional representation of the imaged object or a relevant portion thereof. Assessment of coronary arterial stenosis, for example, would involve generating image data for a volumetric section of the heart including the affected coronary artery.

Tomographic image data for a three-dimensional representation may comprise image data for several slice images at a succession of axial positions (so-called "stacked 2-D slices" or "stacked slice images"). One way to obtain these multiple slice images is to generate corresponding projection data slice by slice by using, for example, a fan beam CT imaging system (such as the system of FIG. 2 or the system of FIG. 3). However, using this approach the collection of the detector data would involve multiple rotations of the gantry for each slice.

Such an operation of multiple rotations for each of multiple slices would require an undesirably long data collection time. In particular, collection of data for all the slices through the heart would be difficult to achieve in one breath hold (20–60 seconds), at least with current CT technology. Another problem is that the patient would receive an undesirably large X-ray dose. Thus, at least for dynamic contexts such as cardiac imaging, the axial scanning arrangements illustrated in FIGS. 2–3 are undesirable.

Figure 7:
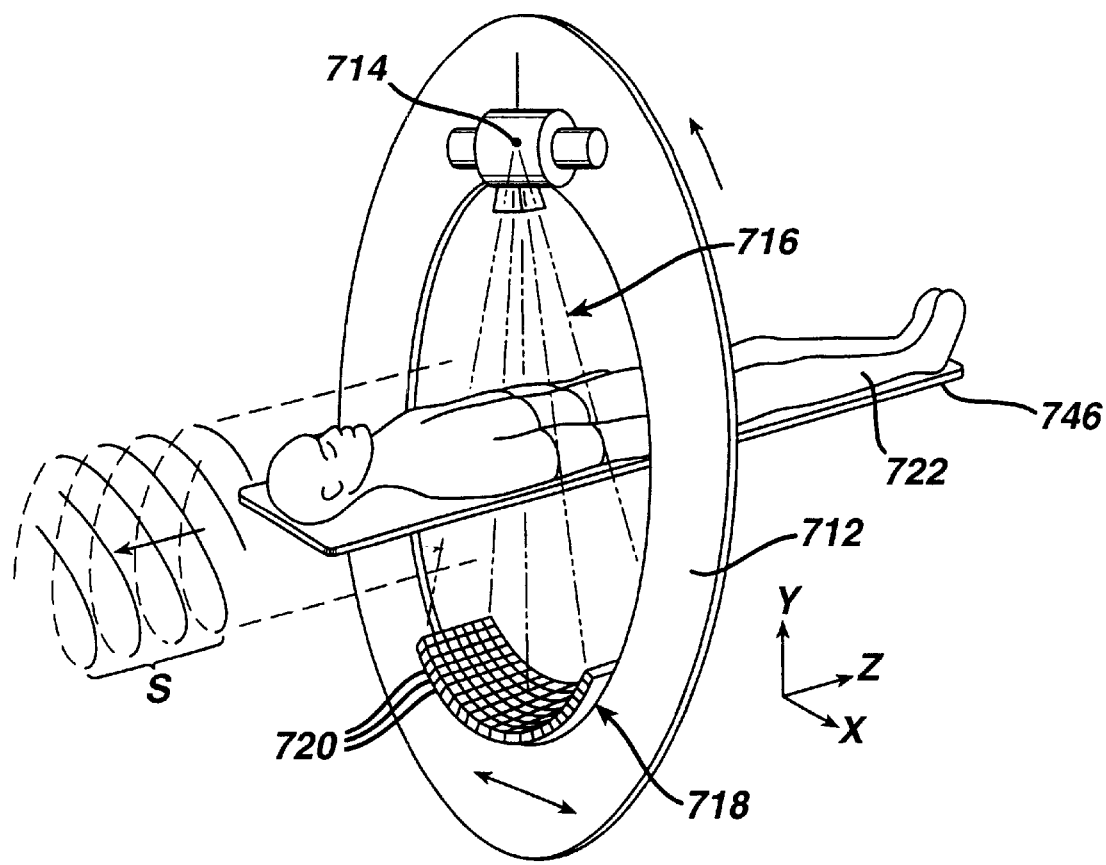
FIG. 7 is a diagram of a source-detector assembly for a helical x-ray CT scanning system using a multi-row detector array.

FIG. 7 illustrates a source-detector assembly 710 for a desirable alternative to axial scanning, called helical scanning. The principal features of assembly 710 are analogous to the components of assemblies 210 and 310 in FIGS. 2 and 3, respectively. A gantry 712 supports an x-ray source 714 that generates an imaging x-ray beam 716. However, unlike the fan beams 216 and 316 described previously, beam 716 is a so-called cone beam that spreads (or "fans") in two generally orthogonal directions as the beam is projected away from the source 714.

The assembly 710 of FIG. 7 corresponds to the third generation axial assembly 210 of FIG. 2. Specifically, the gantry 712 also supports a detector array 718 comprising multiple detector elements 720, and both the source 714 and the detector array 718 are transported around a subject 722 along respective circular paths as the gantry 712 rotates. The detector array 718 is fixed with respect to the source 714 and thereby remains opposite the source 714, relative to the subject 722, during the rotation.

Unlike detector array 218, however, the array 718 is a so-called multi-row detector comprising several rows of detector elements. Each row of the array 718 extends circumferentially with respect to the gantry rotation, and the succession of rows extends axially with respect to the gantry axis of rotation. The array 718 thereby provides a two dimensional detection area, which corresponds to the spread of the cone beam 716 in two complementary directions. This arrangement avoids the need for a complete scanning rotation (i.e., a data acquisition cycle) to be performed at each successive axial position.

Figure 8:
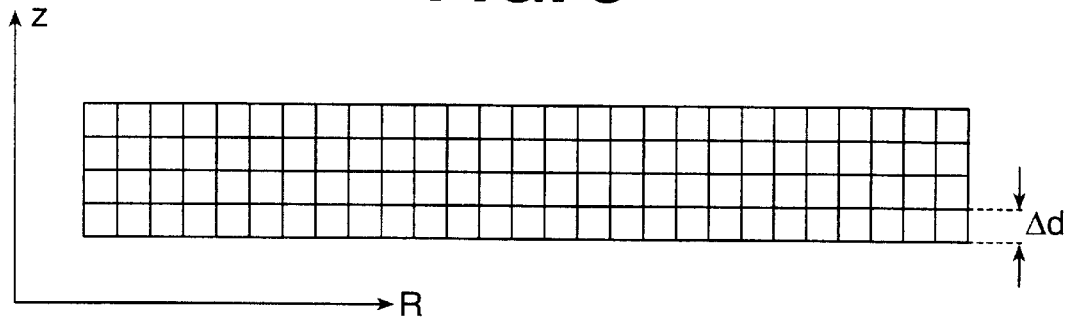
FIG. 8 is a flow diagram illustrating a procedure of the invention.

FIG. 8 shows a schematic diagram of the detector elements of a multi-row detector such as detector array 718. In the illustrated example, each column of the array 718 comprises four detector elements in successive rows of detectors. Thus, instead of providing a row of detector elements at a single axial position $Z_i$, the array 718 comprises several rows arranged successively in the axial direction z. The array 718 can also be characterized as a row of multiple-element columns, with one column occurring at each detector position. Each detector has a thickness of $\Delta_d$ in the z direction. The depiction of four rows is for purposes of illustration and convenience of explanation only. An actual multirow detector may comprise many more that four rows.

Helical scanning relaxes the requirement of axial scanning systems that the axial position if the gantry is fixed at a single point throughout the data collection cycle. Instead, the entire gantry (source and detector array) translates axially (in the z direction) relative to the patient while the gantry is being rotated. A single scanning operation (i.e., continuous rotation of the gantry) can thereby cover the entire organ or structure under study. Moreover, at least in the third generation embodiment of helical scanning, the detector elements 720 trace helical paths around the subject 722.

In the helical scanning case the source 714 also follows a helical path given by $$\theta(0)=\omega t$$

$$Z(0) = (p\Delta_d / 2\pi)\omega t$$

where θ(0) is the view angle, Z(0) is the axial position of the source, and p (for "pitch") is the axial translation per rotation, as a fraction of detector spacing $\Delta_d$.

A useful observation is that the axial positions of some of the detector elements of a multirow array may overlap between successive gantry rotations. If the detector array comprises N rows of detector elements and p<N, then a fill rotation of the detector array θ(0)=0° through θ(0)=360° will advance the array by a distance less than $N\Delta_d$. In other words, when the angle θ(0) returns to 0°, some of the detector rows at the trailing edge will occupy substantially the same axial positions as corresponding rows at the leading edge of the array in the previous rotation.

As time t evolves, the axial position of the m-th detector row at time t can be written as $$z_m(t) = p\Delta_d \frac{\omega t}{2\pi} + m\Delta_d$$
$$= \frac{p\Delta_d}{2\pi}\theta(0) + m\Delta_d$$
$$= Z(0) + m\Delta_d .$$

The angle of the n-th detector column is given by $$\theta_n(t) = \theta(0) + 2\gamma(n) + \pi,$$

where γ(n) is the angle of the n-th detector column relative to the source 714.

A helical/cone beam CT scanning system provides advantages for performing a volumetric reconstruction of the heart. For example, a multi-row detector such as detector array 718 can collect several times more x-ray data from each scanning rotation. The axial position of the cone beam 716 also advances continuously during the scanning operation, so that each detector element 720 traces a helical path around the subject 722. In this manner, the data collection proceeds continuously as the cone beam 716 advances axially, rather than being repeatedly interrupted for a next translation maneuver.

Figure 9:
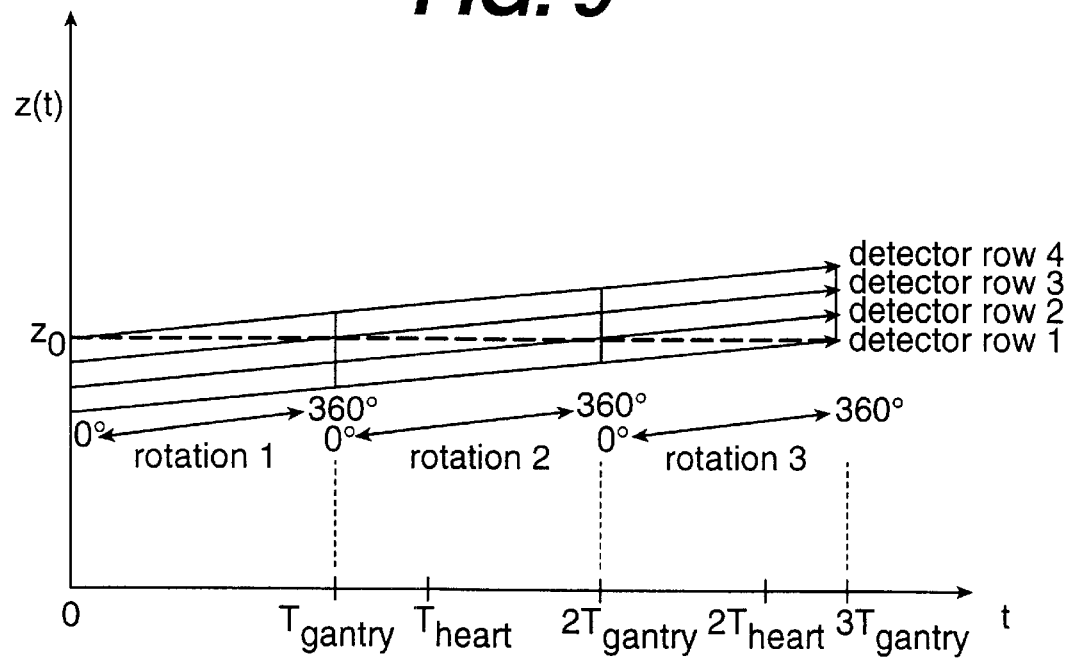
FIG. 9 is a timing diagrams illustrating timing relationships that can be used to select sets of projection data in a preferred application of the present invention for cardiac imaging.

FIG. 9 illustrates that the helical advance of a detector array causes the detector elements to be displaced axially during each rotation. The rotations 1, 2, and 3 represent successive loops of the helical advance of a four-row detector array such as the array 718 as illustrated in FIG. 8. As time t evolves, each gantry rotation advances from a 0° view angle to a 360° view angle. Further, the view angle 360° for a given rotation coincides with the view angle 0° of the succeeding rotation.

The locations of the detector rows of a four-row detector in the z direction are shown in FIG. 9 in the z-t domain. The axial position of each detector row can clearly be seen to change, both between rotations and within each rotation. Still, in each data sample interval dt, each of the detector rows in the multi-row detector defines data corresponding to a proper projection view, i.e., a projection view representing attenuation data for a single axial position.

On the other hand, the interpolation technique noted above is oriented toward independent sets of projection data where each set corresponds to a single axial position z. When the raw data [θ(n), Z(m)] are obtained by helical/cone beam scanning, this entails further processing (rebinning) to assemble the helically skewed data into a sequence of such independent sets for successive axial positions. This rebinning procedure typically entails an interpolation procedure between detector element values of neighboring detector rows.

The present invention proceeds from the further observation that useful information potentially exists in relationships between helical scan data in both space and time. The rebinning procedure noted above illustrates that the spatial proximity of adjacent detector rows has been used to synthesize projection data corresponding to a particular axial position. An aspect of the present invention is the further discovery that the selection of appropriate subsets of the three-dimensional projection data can allow additional information to be extracted from relationships between the raw data collected in different gantry rotations.

One source of this additional information may be the potential for overlap between the helical scan paths of various detector elements in a multirow detector array, as noted above. However, this aspect of the invention also recognizes that other relationships may exist between the raw data of different gantry rotations. A particular instance of such relationships will now be described in conjunction with a preferred embodiment of the invention for volumetric cardiac imaging.

FIG. 10 is a flow diagram illustrating a general procedure provided by the invention. An operation 810 is the basic data collection operation for obtaining three-dimensional projection data. If the projection data are generated with a helical scanning system comprising having a source-detector assembly such as the assembly 710, then the operation may comprise several rotations of the gantry 712 to execute multiple data acquisition cycles. In any case, the operation 810 obtains volumetric projection data representing the imaged object over a plurality of data acquisition cycles.

In an operation 820, the three-dimensional projection data are analyzed to determine (for example, to select) a particular set of projection views at a selected view angle for each data acquisition cycle. It is desirable to select the view angles for this operation 820 according to a time dependent feature of the object being imaged. The particular sets of projection views may then be selected to satisfy a predetermined relationship for the time dependent feature between the different sets. A particular case of this determining operation will be described below with reference to FIGS. 13–15.

An operation 830 provides a reconciliation between the axial positions at which the projection views of a given set represent the object and the axial positions at which the stacked slice images are to represent the object. This reconciliation is typically helpful because the helical projection data are axially skewed within each rotation data set. Thus, with reference to FIG. 9, it will be likely that none of the detector rows will coincide in axial position with a specified position, at least when the view angle θ is chosen according to some other criterion. Thus, to generate projection views representing the object at the specified axial position, a spatial interpolation is typically carried out in the operation 830.

An operation 840 generally completes the procedure by reconstructing a number (usually several, but possibly only one or two) slice images at the respective specified axial positions. For each slice image, this operation entails selecting projection views from respective ones of the sets of projection views (or from the reconciled sets of projection views). In this way, each slice image may be reconstructed from several projection views representing the object at different view angles but at the same specified axial position.

A particular embodiment of the present invention will now be described in the context of cardiac imaging. Persons of skill in the art will appreciate, however, that the invention can also be applied in other medical and non-medical imaging contexts where a time dependent feature of the three dimensional projection data implicitly carries additional information about the imaged object.

As noted above, a fundamental problem in cardiac tomographic imaging is to generate a number of consistent projection views to reconstruct a tomographic image of the cardiac structures with high resolution and few noise and artifact features. In the simplest case, it may be assumed that the heart rate is constant while the scan data are collected. The desired shape configuration (or "phase") then occurs in each cardiac cycle at a fixed fraction of the heart period $T_h$ following the preceding R-wave. For a given cardiac cycle, a projection view corresponding to the desired heart phase may be identified by reference to the fixed fraction and the time stamps correlating to the cardiac R-wave that begins the cardiac cycle.

The assumption of regular heartbeat simplifies the process of cross-referencing the projection data and the EKG data. In particular, for each R-R heart cycle the desired phase of the heart occurs at the same time to after the R-wave of the cycle. The simplifying assumption of regular heart rate thus creates an assumed correlation between the time stamps of the row data and the respective phases of the cardiac cycle.

However, usually the heart rate is not uniform during the data acquisition process. The preferred procedure is then to collect an electrocardiogram (EKG) data set along with the helical scan data. The EKG data set can then be correlated off-line with CT scan data, using the time stamps associated with the raw volumetric projection data. Thereafter, using the time stamps and the correlations to the EKG data, the particular projection data corresponding to a selected cardiac configuration phase can be identified.

Such an adaptation to heart rate variations is well known in the art and has been used, for example, in the sector approach described above with respect to FIG. 6. Persons skilled in the art will readily appreciate the appropriate measures to be used with the present invention to compensate for the presence of heart rate variability. For example, a compensation model is employed in the technique of U.S. Pat. No. 5,997,883 to Epstein et al. noted previously.

On the other hand, an embodiment of the present invention is particularly useful in cases where heart rate variability exists. It is known that in most cases where the heart cycle duration varies, the systole period of the cardiac cycle is relatively stable. In other words, the portion of the cardiac cycle that changes,in duration most commonly is the diastole period, when the heart is in a relaxed state. This fact can be used to develop a selection criterion for selecting sets of projection views, as in the operation 820 of FIG. 8.

FIGS. 11A–11C are timing diagrams that illustrate the determination of a trigger delay TD with which to select the projection data sets. In FIG. 11A, the R waves of successive cardiac cycles occur at irregular times, due to the heart rate variability. FIG. 11B shows the corresponding displacement of a coronary artery to be imaged. During the systole period, the displacement is substantial and will tend to create motion inconsistencies in the projection data. However, if a fixed time TD is measured after each R wave, it can be seen that the heart has entered the quiescent diastole period. As FIG. 11B illustrates, the duration of the diastole period may vary substantially from cardiac cycle to cardiac cycle. However, the entering portion of the diastole occurs reliably at the delay time TD after the R wave.

FIG. 11C illustrates the timing of trigger signals by which to select the sets of projection views from the three-dimensional projection data. By generating a trigger signal at a fixed trigger delay TD after each R wave, sets of projection views can be selected from the volumetric data to represent the heart in a same phase of the cardiac cycle. The trigger delay can be chosen so that the particular phase is a phase at which the heart is nearly still, thereby enhancing the consistency of the selected projection data sets. Different trigger delays can be used to generate a four-dimensional model of the heart.

Figure 12:
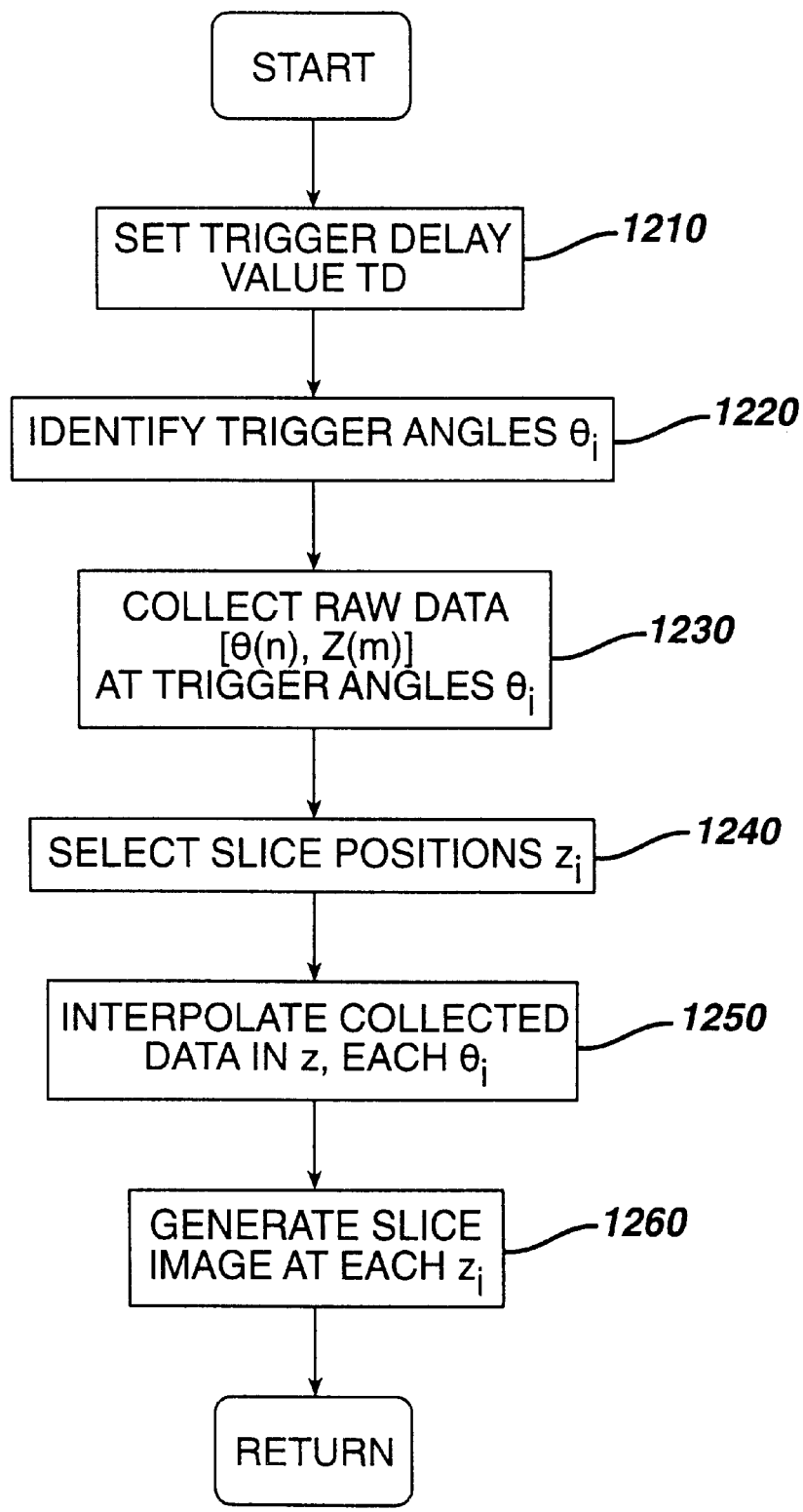
FIG. 12 is a time evolution diagram of the detector row positions shown in FIG. 11 with sets of projection views indicated at selected view angles.

FIG. 12 is a flow diagram illustrating a procedure of the invention as applied in the foregoing context of cardiac imaging. A trigger delay TD is set to a specific value in an operation 1210, thereby determining the particular phase of the heart for the three-dimensional image reconstruction.

As can be seen from FIG. 9, the trigger delay TD will typically correspond to a different view angle θ for each of the scanning rotations (data acquisition cycles ROTATION 1, ROTATION 2, etc.). An operation 1220 therefore identifies the trigger angles $θ_I$ for the corresponding rotational data sets. An operation 1230 collects the raw data [θ(n), Z(m)] at the corresponding trigger angles $θ_I$, using the time stamp correlations between the EKG data and the projection data.

An operation 1240 selects the axial positions $Z_i$ at which the one or more slice images are to be reconstructed. The positions $Z_i$ may be chosen to coincide with the successive axial positions of one of the selected projection data sets, although the helical skew of the volumetric projection data will generally prevent such coincidence for the other sets. An operation 1250 then completes the reconciliation of the axial positions of the selected projection data sets with the specified axial positions for the slice images, by interpolating the collected projection data sets in z. The reconciled projection data sets can then be input to the reconstruction process to generate the desired slice images.

Figure 13:
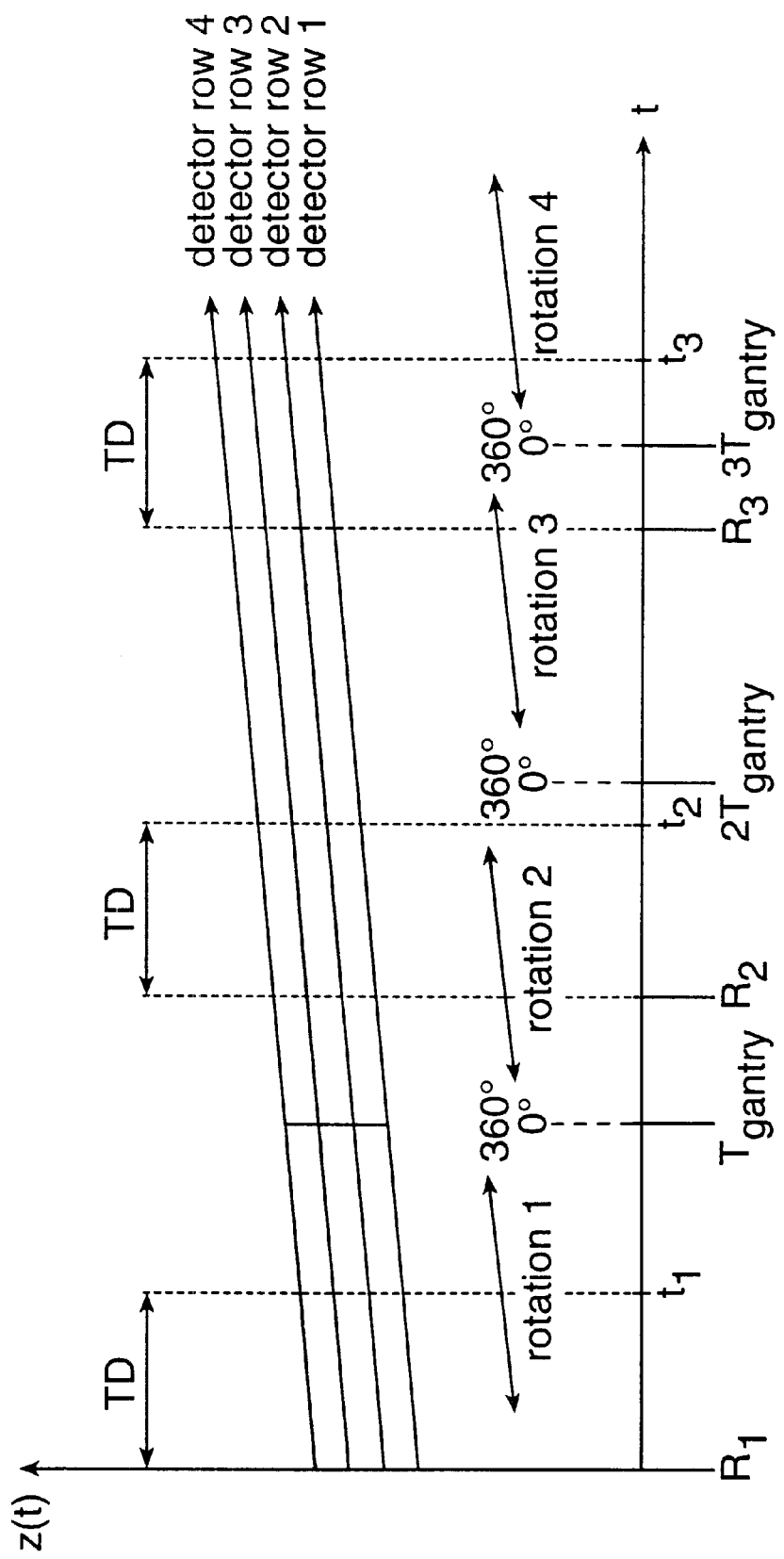
FIG. 13 is a diagram of axial position versus view angle showing the selected sets of projection views from FIG. 12.

FIG. 13 shows a time evolution diagram similar to the diagram of FIG. 9, but with the trigger delay TD indicated after the R waves $R_1$, $R_2$, and $R_3$. In the illustrated example, the gantry rotation period $T_{gantry}$ is less than the nominal period of the cardiac cycle. Therefore, triggers $t_1$, and $t_2$ occur in rotations 1 and 2, respectively, but trigger $t_3$ does not occur until rotation 4. A different choice for TD would result in different locations of the triggers $t_i$.

Figure 14:
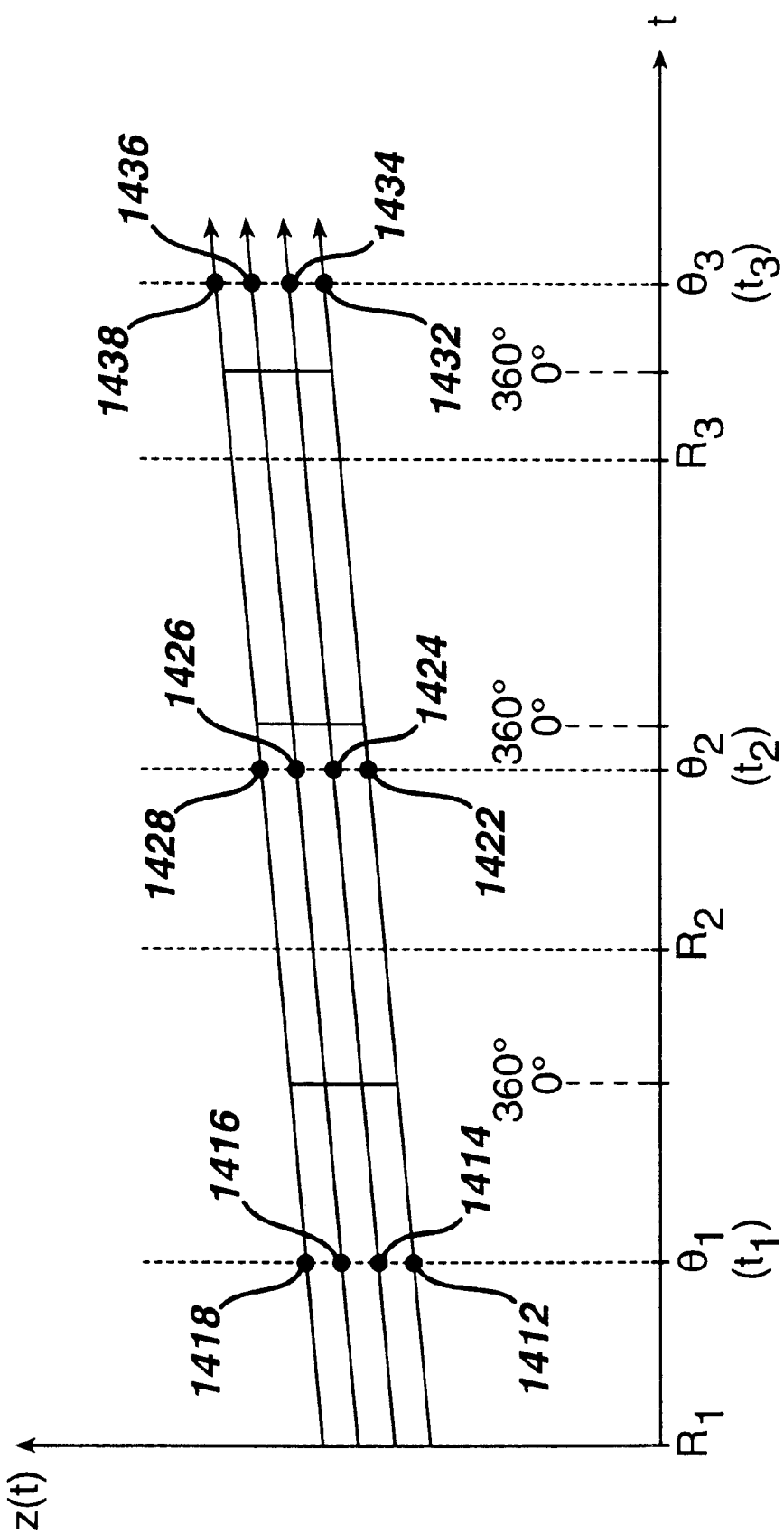
FIG. 14 is a diagram of axial position versus view angle showing corresponding sets of projection views in the time stamped projection data.

FIG. 14 shows that the triggers $t_i$ determine trigger angles $θ_i$ in the rotations 1, 2, and 4. Each selected trigger angle $θ_i$ determines a corresponding set of projection views in the time stamped projection data. For example, $θ_1$ determines the projection views 1412, 1414, 1416, and 1418, which happen to correspond to the first through fourth detector rows of the multi-row detector array. The trigger angle $θ_2$ determines the projection views 1422, 1424, 1426, and 1428 from rotation 2. The trigger angle $θ_3$ determines the projection views 1432, 1434, 1436, and 1438 from rotation 4. A notable point is that all of the projection views 1412 through 1438 represent the imaged heart in the same phase of the cardiac cycle. This is achieved by determining the sets of projection views from the raw data, rather than selecting a specified axial position for the desired image and then searching for suitable projection views in the raw data.

Figure 15:
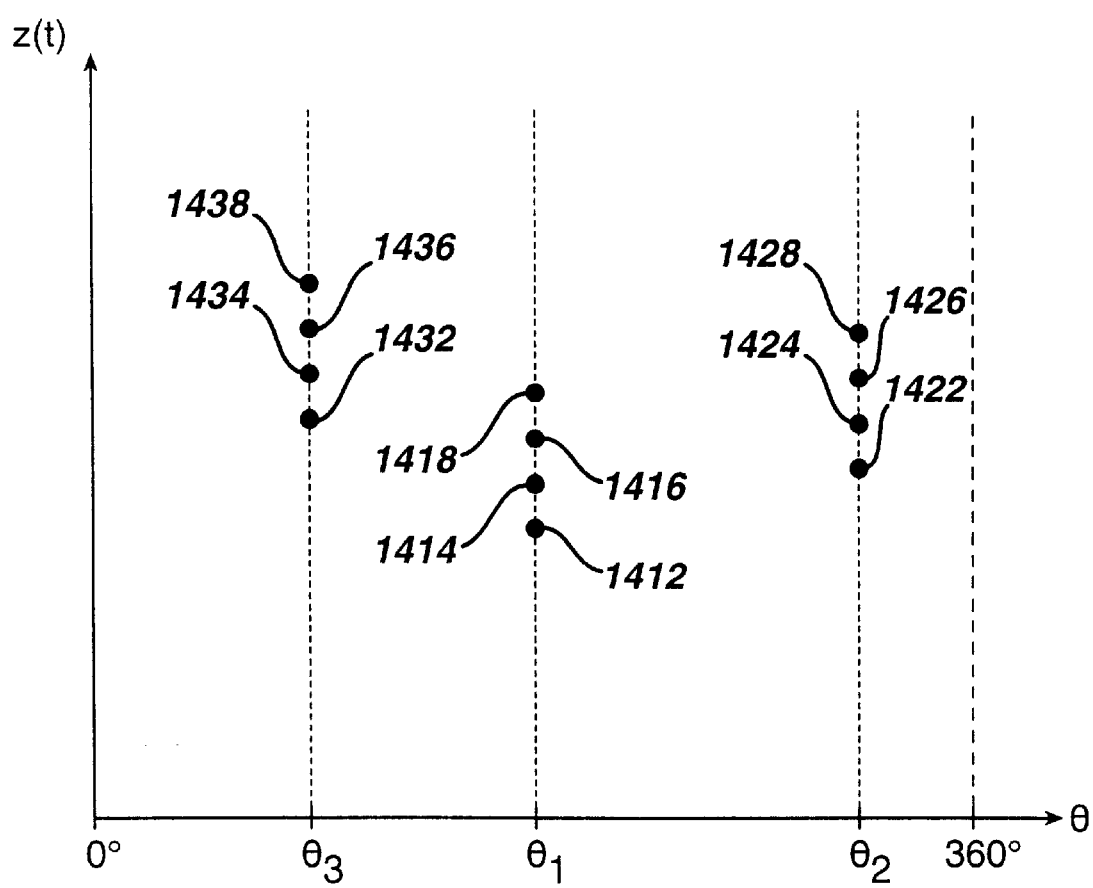
FIG. 15 is a diagram of selected sets of projection views at their respective view angles relative to a single cycle of view angles.

FIG. 15 shows the selected sets of projection views at their respective view angles relative to a single cycle of view angles θ. Due to the axial skewing of the raw projection data, the several projection views 1412 through 1438 correspond to different axial positions z. Reconstruction of a slice image at a specified axial position therefore will typically entail reconciliation of the selected projection view sets. A reconciled set of projection views is thereby selected to representing the heart at the same view angles $θ_1$ through $θ_3$, but at a single specified axial position z.

Various implementations of the invention described herein above have been tested with clinical cardiac data. These results demonstrate that the invention can noticeably reduce the streaks and other artifacts that occur when the sector approach is applied.

As this invention may be embodied in several forms without departing from the spirit or principal characteristics thereof, the present embodiments are therefore illustrative and not restrictive. Those skilled in the art will appreciate that changes may be made to these embodiments without departing from the principles and spirit of the invention. Accordingly, the scope of the invention is defined by the appended claims rather than by the description preceding them, and all changes that fall within the metes and bounds of the claims, or equivalents of such metes and bounds thereof, are therefore intended to be embraced by the claims.

What is claimed is:

1. A tomographic image generation method, comprising:
   determining plural sets of projection views of an object based on projection data from respective different data acquisition cycles, each set comprising plural projection views of the object at a corresponding view angle and at successive positions on an axis; and
   reconstructing a slice image of the object at a specified position on the axis based on a plurality of projection views selected from respective ones of the plural sets;
   wherein for each of the plural sets of projection views the corresponding view angle is different from the corresponding view angle of the projection views of each of the other sets.

2. A method as recited in claim 1, wherein all of the plural sets consist of a same number of projection views.

3. A method as recited in claim 1, further comprising reconstructing another slice image of the object at an axial position adjacent to the specified position on the axis and based on projection views selected from respective ones of the plural sets.

4. A method as recited in claim 1, wherein the respective different data acquisition cycles are consecutive data acquisition cycles.

5. A method as recited in claim 1, wherein the projection data are data based on detector data collected by a tomographic imaging system while the object is in motion.

6. A method as recited in claim 5, wherein the motion of the object is cyclical motion.

7. A method as recited in claim 6, wherein successive cycles of the cyclical motion have a same cycle period.

8. A method as recited in claim 6, wherein successive cycles of the cyclical motion each has a cycle duration within a range of variation below or above a nominal cycle period.

9. A method as recited in claim 1, wherein:
   the object is in cyclical motion during the data acquisition cycles; and
   the determining operation comprises selecting the projection views of the plural sets to represent the object at a same specified phase of the cyclical motion.

10. A method as recited in claim 1, wherein the projection data represent intensities of energetic rays transmitted through the object.

11. A method as recited in claim 1, further comprising selecting the plurality of selected projection views to comprise at least one projection view from each of the plural sets.

12. A method as recited in claim 1, further comprising:
   selecting the plurality of selected projection views to comprise two projection views of the object at adjacent positions on the axis from a same one of the plural sets, the specified position being collinear with and between the adjacent positions; and
   interpolating between the two projection views with respect to position on the axis to generate for use in the reconstruction operation an interpolated projection view of the object at the corresponding view angle and at the specified position on the axis.

13. A method as recited in claim 1, wherein the plural sets of projection views are determined based on timing data collected contemporaneously with the data acquisition cycles.

14. A method as recited in claim 1, wherein the projection data are data based on detector data collected by an x-ray detector array disposed at least in part on a side of the axis opposite an x-ray source rotating around the object and emitting x-rays toward the detector array.

15. A method as recited in claim 1, further comprising:
   collecting detector data with an x-ray detector array disposed at least in part on a side of the axis opposite an x-ray source rotating around the object and emitting x-rays toward the detector array; and
   generating the projection data based on the collected detector data.

16. A method as recited in claim 1, wherein the projection data are data based on detector data collected by an x-ray detector array.

17. A method as recited in claim 1, wherein:
   the projection data are data based on detector data collected by a multiple-row x-ray detector array disposed at least in part on a side of the axis opposite an x-ray source; and
   the data acquisition cycles are scanning rotations each comprising rotation of the x-ray source around the object while emitting x-rays toward the detector array.

18. A method as recited in claim 1, wherein:
   the object is in cyclical motion during the data acquisition cycles; and
   a cycle duration of the data acquisition cycles is different from a cycle duration of successive cycles of the cyclical motion.

19. A method as recited in claim 1, wherein:
   the object is in cyclical motion during the data acquisition cycles; and
   the cyclical motion comprises successive cycles of at least one of translation, rotation, and elastic deformation of the object.

20. A method as recited in claim 1, wherein the object is an organ of a living subject.

21. A method as recited in claim 1, wherein the subject is a mammal and the organ is the subject's heart.

22. A method according to claim 1, wherein the detector data represent intensities of energetic rays transmitted through the object.

23. A method according to claim 22, wherein the energetic rays comprise x-rays.

24. A computer-readable medium encoded with a program for performing tomographic image generation, said program comprising instructions for:
   determining plural sets of projection views of an object based on projection data from respective different data acquisition cycles, each set comprising plural projection views of the object at a corresponding view angle and at successive positions on an axis; and
   reconstructing a slice image of the object at a specified position on the axis based on a plurality of projection views selected from respective ones of the plural sets;

wherein said program further comprises instructions for selecting the plurality of selected projection views to comprise at least one projection view from each of the plural sets.

25. A computer-readable medium as recited in claim 24, wherein said program further comprises instructions for reconstructing another slice image of the object at an axial position adjacent to the specified position on the axis and based on projection views selected from respective ones of the plural sets.

26. A computer-readable medium as recited in claim 24, wherein the projection data are data based on detector data collected by a tomographic imaging system while the object is in motion.

27. A computer-readable medium as recited in claim 24, wherein:
   the object is in cyclical motion during the data acquisition cycles; and
   the determining instructions of said program comprise instructions for selecting the projection views of the plural sets to represent the object at a same specified phase of the cyclical motion.

28. A computer-readable medium as recited in claim 24, wherein said program further comprises instructions for:
   selecting the plurality of selected projection views to comprise two projection views of the object at adjacent positions on the axis from a same one of the plural sets, the specified position being collinear with and between the adjacent positions; and
   interpolating between the two projection views with respect to position on the axis to generate for use in the reconstruction operation an interpolated projection view of the object at the corresponding view angle and at the specified position on the axis.

29. A computer-readable medium as recited in claim 24, wherein the instructions of said program comprise instructions for determining the plural sets of projection views based on timing data collected contemporaneously with the data acquisition cycles.

30. A computer-readable medium as recited in claim 24, wherein said program further comprises instructions for:
   collecting detector data with an x-ray detector array disposed at least in part on a side of the axis opposite an x-ray source rotating around the object and emitting x-rays toward the detector array; and
   generating the projection data based on the collected detector data.

31. A tomographic cardiac imaging method, comprising:
   generating a plurality of x-ray projection data sets based on detector data collected in respective different data acquisition cycles, each projection data set comprising plural projection views of a subject's heart at a corresponding view angle and at successive positions on an axis of rotation through the subject; and
   reconstructing a plurality of stacked slice images based on respective projection view sets each comprising projection views selected from respective ones of tie projection data sets, each slice image representing the patient's heart at a corresponding position on the axis and the plurality of stacked slice images together depicting at least a three-dimensional portion of the subject's heart;
   wherein for each of the plurality of projection data sets the corresponding view angle is different from the corresponding view angle of the projection views of each of the other projection data sets.

32. A method as recited in claim 31, wherein the projection views of the projection data sets represent the patient's heart at a same specified phase of the heart's cardiac cycle.

33. A method as recited in claim 31, further comprising selecting the plurality of selected projection views for each of the slice images to comprise at least one projection view from each of the plurality of projection data sets.

34. A method as recited in claim 31, further comprising:
   selecting the plurality of selected projection views for a specific slice image representing the heart at a corresponding axial position to comprise two projection views of the patient's heart at adjacent positions on the axis from a same one of the projection data sets, the corresponding axial position being collinear with and between the adjacent positions; and
   interpolating between the two projection views with respect to position on the axis to generate an interpolated projection view of the subject's heart at the corresponding view angle and at the corresponding axial position.

35. A method as recited in claim 31, further comprising:
   generating timing data indicating successive cardiac cycles of the subject's heart occurring contemporaneously with the data acquisition cycles; and
   determining the plurality of projection data sets based on the timing data.

36. A method as recited in claim 31, wherein the detector data are data collected by a multiple-row x-ray detector array disposed at least in part on a side of the axis opposite an x-ray source rotating around the object and emitting x-rays toward the detector array.

37. A method as recited in claim 31, further comprising:
   collecting the detector data with an x-ray detector array disposed at least in part on a side of the axis opposite an x-ray source rotating around the object and emitting x-rays toward the detector array; and
   generating the plural projection data sets based on the collected detector data.

38. A tomographic image generation device, comprising:
   at least one storage to store x-ray projection data comprising a plurality of projection data sets based on detector data collected in respective different data acquisition cycles, each projection data set comprising plural projection views of a subjection heart at a corresponding view angle and at successive positions on an axis of rotation through the subject; and
   at least one processor to determine the plural sets of projection views of the object and to reconstruct a plurality of stacked slice images based on respective projection view sets each comprising projection views selected from respective ones of the projection data sets, each slice image representing the patient's heart at a corresponding position on the axis and the plurality of stacked slice images together depicting at least at dimensional portion of the subject's heart;
   wherein said at least one processor determines each of the plurality of projection data sets to correspond to a view angle different from the corresponding view angle of the projection views of each of the other projection data sets.

39. A device as recited in claim 38, wherein said at least one processor determines the projection views of the projection data sets to represent the patient's heart at a same specified phase of the heart's cardiac cycle.

40. A device as recited in claim 38, wherein said at least one processor selects the plurality of selected projection views for each of the slice images to comprise at least one projection view from each of the plurality of projection data sets.

41. A device as recited in claim 38, wherein for a specific slice image representing the heart at a corresponding position on the axis:
said at least one processor selects the respective projection view set to comprise two projection views of the patient's heart at adjacent positions on the axis from a same one of the projection data sets, the corresponding position being collinear with and between the adjacent positions; and
said at least one processor interpolates between the two projection views with respect to position on the axis to generate an interpolated projection view of the subject's heart at the corresponding view angle and at the corresponding position.

42. A device as recited in claim 38, further comprising:
a timing data acquisition system to generate timing data indicating successive cardiac cycles of the subject's heart occurring contemporaneously with the data acquisition cycles; and
a trigger signal generator to generate trigger signals based on the timing data for determining the plurality of projection data sets.

43. A device as recited in claim 42, wherein said timing data acquisition system comprises an electrocardiograph.

44. A device as recited in claim 38, wherein the detector data are data collected by a multiple-row x-ray detector array disposed at least in part on a side of the axis opposite an x-ray source rotating around the object and emitting x-rays toward the detector array.

45. A device as recited in claim 38, wherein:
the detector data are data collected with an x-ray detector array disposed at least in part on a side of the axis opposite an x-ray source rotating around the object and emitting x-rays toward the detector array; and
said at least one processor generates the plural projection data sets based on the collected detector data.

46. A tomographic imaging system, comprising;
a detector array to detect energetic rays originating from a calibrated source and transmitted through or emitted from an object in a plurality of data acquisition cycles;
at least one storage to store projection data based on detector data from said detector array, the projection data comprising a plurality of x-ray projection data sets based on detector data collected in respective different data acquisition cycles, each projection data set comprising plural projection views of a subject's heart at a corresponding view angle and at successive positions on an axis of rotation through the subject;
at least one processor to determine plural projection view sets each comprising projection views selected from respective ones of the projection data sets; and
a reconstruction engine to reconstruct a plurality of stacked slice images each representing the patient's heart at a corresponding position on the axis and the plurality of stacked slice images together depicting at least a three-dimensional portion of the subject's heart;
wherein said at least one processor determines each of the plurality of projection data to correspond to a view angle different from the corresponding view angle of the projection views of each of the other projection data sets.

47. A system as recited in claim 46, wherein said at least one processor determines the projection views of the projection data sets to represent the patient's heart at a same specified phase of the heart's cardiac cycle.

48. A system as recited in claim 46, wherein said at least one processor selects the plurality of selected projection views for each of the slice images to comprise at least one projection view from each of the plurality of projection data sets.

49. A system as recited in claim 46, wherein for a specific slice image representing the heart at a corresponding position on the axis:
said at least one processor selects the respective projection view set to comprise two projection views of the patient's heart at adjacent positions on the axis from a same one of the projection data sets, the corresponding position being collinear with and between the adjacent positions; and
said at least one processor interpolates between the two projection views with respect to position on the axis to generate an interpolated projection view of the subject's heart at the corresponding view angle and at the corresponding position.

50. A system as recited in claim 46, further comprising:
a timing data acquisition system to generate timing data indicating successive cardiac cycles of the subject's heart occurring contemporaneously with the data acquisition cycles; and
a trigger signal generator to generate trigger signals based on the timing data for determining the plurality of projection data sets.

51. A system as recited in claim 50, wherein said timing data acquisition system comprises an electrocardiograph.

52. A system as recited in claim 46, wherein said detector array is a multiple-row x-ray detector array disposed at least in part on a side of the axis opposite an x-ray source rotating around the object and emitting x-rays toward the detector array.

53. A system as recited in claim 46, wherein:
said detector array is an x-ray detector array disposed at least in part on a side of the axis opposite an x-ray source rotating around the object and emitting x-rays toward the detector array; and
said at least one processor generates the plural projection data sets based on the collected detector data.

54. A computer-readable medium encoded with a program for performing tomographic cardiac imaging, said program comprising instructions for:
generating a plurality of x-ray projection data sets based on detector data collected in respective different data acquisition cycles, each projection data set comprising plural projection views of a subject's heart at a corresponding view angle and at successive positions on an axis of rotation through the subject; and
reconstructing a plurality of stacked slice images based on respective projection view sets each comprising projection views selected from respective ones of the projection data sets, each slice image representing the patient's heart at a corresponding position on the axis and the plurality of stacked slice images together depicting at least a three-dimensional portion of the subject's heart;
wherein the instructions for determining each of the plurality of projection data sets to correspond to a view angle different from the corresponding view angle of the projection views of each of the other projection data sets.

55. A computer-readable medium as recited in claim 54, wherein the projection views of the projection data sets represent the patient's heart at a same specified phase of the heart's cardiac cycle.

56. A computer-readable medium as recited in claim 54, wherein said program further comprises instructions for selecting the plurality of selected projection views for each of the slice images to comprise at least one projection view from each of the plurality of projection data sets.

57. A computer-readable medium as recited in claim 54, wherein said program further comprises instructions for:

selecting the plurality of selected projection views for a specific slice image representing the heart at a corresponding axial position to comprise two projection views of the patient's heart at adjacent positions on the axis from a same one of the projection data sets, the corresponding axial position being collinear with and between the adjacent positions; and interpolating between the two projection views with respect to position on the axis to generate an interpolated projection view of the subject's heart at the corresponding view angle and at the corresponding axial position.

58. A computer-readable medium as recited in claim 54, wherein said program further comprises instructions for:

generating timing data indicating successive cardiac cycles of the subject's heart occurring contemporaneously with the data acquisition cycles; and determining the plurality of projection data sets based on the timing data.

59. A computer-readable medium as recited in claim 54, wherein the detector data are data collected by a multiple-row x-ray detector array disposed at least in part on a side of the axis opposite an x-ray source rotating around the object and emitting x-rays toward the detector array.

60. A computer-readable medium as recited in claim 54, wherein said program further comprises instructions for:

collecting the detector data with an x-ray detector array disposed at least in part on a side of the axis opposite an x-ray source rotating around the object and emitting x-rays toward the detector array; and generating the plural projection data sets based on the collected detector data.

* * * * *